(12) United States Patent
Stegmann

(10) Patent No.: US 12,350,168 B2
(45) Date of Patent: Jul. 8, 2025

(54) INTERVERTEBRAL FUSION CAGE

(71) Applicant: Johann Petrus Stegmann, Germiston (ZA)

(72) Inventor: Johann Petrus Stegmann, Germiston (ZA)

(*) Notice: Subject to any disclaimer, the term of this patent is extended or adjusted under 35 U.S.C. 154(b) by 782 days.

(21) Appl. No.: 17/614,776

(22) PCT Filed: May 29, 2020

(86) PCT No.: PCT/IB2020/055117
§ 371 (c)(1),
(2) Date: Nov. 29, 2021

(87) PCT Pub. No.: WO2020/240496
PCT Pub. Date: Dec. 3, 2020

(65) Prior Publication Data
US 2022/0226126 A1 Jul. 21, 2022

(30) Foreign Application Priority Data
May 31, 2019 (NL) ........................... 2023241

(51) Int. Cl.
*A61F 2/44* (2006.01)
*A61F 2/28* (2006.01)
*A61F 2/30* (2006.01)
*A61F 2/46* (2006.01)

(52) U.S. Cl.
CPC .......... *A61F 2/4455* (2013.01); *A61F 2/4611* (2013.01); *A61F 2002/2835* (2013.01); *A61F 2002/30593* (2013.01); *A61F 2002/30904* (2013.01); *A61F 2002/4622* (2013.01); *A61F 2002/4627* (2013.01)

(58) Field of Classification Search
CPC ................................. A61F 2/44–447
See application file for complete search history.

(56) References Cited

U.S. PATENT DOCUMENTS

| | | | | |
|---|---|---|---|---|
| 5,776,199 A * | 7/1998 | Michelson | ............ | A61F 2/4455 606/247 |
| 6,592,624 B1 * | 7/2003 | Fraser | ..................... | A61F 2/442 623/17.16 |
| 8,840,622 B1 * | 9/2014 | Vellido | ................. | A61F 2/4611 606/86 A |

(Continued)

FOREIGN PATENT DOCUMENTS

DE 202005018655 U1 1/2006

*Primary Examiner* — Nicholas J Plionis
(74) *Attorney, Agent, or Firm* — WCF IP

(57) ABSTRACT

This invention relates to an intervertebral fusion cage for insertion between vertebrae. The cage has a body defining a first, anterior portion, a second, posterior portion and a central portion extending between the anterior and posterior portions. The central portion may define a first surface which is, in use, a top surface and a second surface which is, in use, a bottom surface. The top and bottom surfaces may carry gripping formation for gripping end plates of the vertebrae. The gripping formations on the top and bottom surfaces preferably face substantially opposite directions such that the gripping formations on the top surface obstruct movement in first direction while the gripping formations on the bottom surface obstruct movement in a second direction, which is substantially opposite the first direction.

19 Claims, 14 Drawing Sheets

(56) References Cited

U.S. PATENT DOCUMENTS

| | | |
|---|---|---|
| 2001/0031969 A1 | 10/2001 | Aebi et al. |
| 2003/0055434 A1 | 3/2003 | O'Neil |
| 2003/0074063 A1* | 4/2003 | Gerbec ............... A61F 2/4611 623/16.11 |
| 2003/0225416 A1 | 12/2003 | Bonvallet et al. |
| 2004/0127990 A1* | 7/2004 | Bartish, Jr. ............ A61F 2/4465 623/17.11 |
| 2004/0176852 A1* | 9/2004 | Zubok ............... A61F 2/4611 623/17.11 |
| 2005/0165408 A1 | 7/2005 | Puno et al. |
| 2008/0287957 A1 | 11/2008 | Hester et al. |
| 2009/0005870 A1 | 1/2009 | Hawkins |
| 2010/0160983 A1* | 6/2010 | Runco ............... A61F 2/4611 606/86 A |
| 2011/0082555 A1 | 4/2011 | Martz et al. |
| 2016/0051371 A1 | 2/2016 | Defelice et al. |
| 2017/0065269 A1* | 3/2017 | Thommen .......... A61B 1/00154 |

\* cited by examiner

INTERVERTEBRAL FUSION CAGE

RELATED APPLICATIONS

This application claims priory from Dutch patent application no. 2023241 filed on 31 May 2019 entitled "Intervertebral Fusion Cage", the content of which is incorporated herein in its entirety.

BACKGROUND TO THE INVENTION

THIS invention relates to an intervertebral fusion cage. The invention further relates to a method of conducting a fusion of vertebrae using the cage, and in particular to a method of inserting such cage.

An intervertebral fusion cage is typically inserted between two adjacent vertebrae of a patient as part of spinal corrective surgery, such as spinal fusion (also referred to as spondylodesis or arthrodesis). Spinal fusion can be performed in the cervical, thoracic and lumbar regions of the spine to prevent movement between the fused vertebrae. Spinal fusion surgery includes packing the cage with bone graft material and inserting the packed cage between the adjacent vertebrae. The packed cage assists with the separation of the vertebrae while the bone graft fuses to the vertebrae end plates, thereby fusing the vertebrae together. Other stabilising means such as pedicle screws and rods are almost always used in addition to the cage to stabilise the vertebrae so as to maintain the correct position between the cage and vertebrae while the bone graft fuses to the vertebrae end plates.

Many variations of intervertebral fusion cages have been proposed and are currently available in the market. For example, a known trans facet lumbar interbody fusion (TLIF) cage is shown in FIG. 2(a) and a known posterior lumbar interbody fusion (PLIF) cage is shown in FIG. 2(b). A known crescent type cage, which is inserted obliquely and then rotated to lie diagonally across the disc space, is shown in FIG. 3. The bullet part of the cage does not make contact with the endplate and the anterior rim of the cage comes to lie behind the cortical rim. Considering the designs of these cages and where they come to rest in use between the vertebrae there are many significant disadvantages associated with these known cages. For example, problems such as subsidence, inadequate restoration of lordosis and disc space height, difficulties with reduction of spondylolisthesis, non-union or unsuccessful fusion, difficulties and safety problems in cage placement, and cage migration and movement are often experienced.

Subsidence is the act or process whereby the cage collapses into a vertebral body through its bony endplate. In practice, when subsidence occurs, the cage more often than not collapses through the end plate of the vertebra above the cage. Subsidence typically results in a loss of height restoration, a decrease or loss of lordosis, pain due to endplate fracture and loss of adequate support to be provided by the cage, which could result in less probability of fusion to occur. The causes of subsidence include damage to the bony endplate during evacuation of the disc space and removal of the cartilage end plate causing a weakness in the bony support of the cage, a small surface area of the cage leading to a concentration of forces over a small area, the cage resting predominantly or exclusively on the thickened cancellous portion of the vertebral endplate instead of the stronger cortical bony rim, osteoporosis, irregular concentration of forces by the cage on the bone as a result of surface geometry mismatches, lift type cages causing excessive force on endplate leading to fracture and the material from which the cage is manufactured having a modulus of elasticity significantly different from that of the vertebral bone e.g. Titanium and Tantalum.

The bony vertebral endplate consist of an inner thickened cancellous bone part and an outer rim of stronger cortical bone. The inner part is concave with the inferior endplate, i.e. the endplate of the vertebra above the cage, being more concave than the superior endplate, i.e. the endplate of the vertebra below the cage. The inferior cancellous endplate is weaker than the superior endplate. The outer cortical rim is convex with the inferior endplate being more convex than the superior endplate cortical rim. Known cages allow for placement of the cage against the softer cancellous endplate with possibly some minor contact against the inner part of the cortical rim. This is not ideal and may lead to an increased risk of subsidence and an inadequate ability to restore height and achieve lordosis.

Lumbar and cervical lordosis is vitally important to maintain sagittal balance of the spine. Spinal degeneration leads to decrease and/or loss of lordosis and disc height resulting in pain, probably accelerated adjacent level degeneration, deformity and increased fatigue of spinal muscles. Spinal surgery aims to restore or maintain lordosis. If this is not performed adequately and correctly, numerous problems may result, such as unsuccessful surgery with continued or worsening pain, increased stress forces on the adjacent spinal levels theoretically causing accelerated degeneration and, accordingly, reoperation. Height restoration anteriorly of the intervertebral space increase lordosis and indirectly decompress the spinal nerve canal and foramina removing compression on spinal nerves.

Spondilolisthesis is a common lumbar spine condition causing spinal stenosis of the central canal, lateral recess and foramens. This results in nerve root compression. There is usually associated facet joint degeneration present. The result is nerve root pain, neurologic deficit, neurogenic claudication and/or back pain. If these symptoms are severe enough, surgery is required. Surgery aims to relieve nerve compression, reduce the listhesis and restore height. This is typically achieved by performing a fusion and decompression.

Listhesis is graded according to degree of slip of the superior vertebra. In practice, most of the listhesis is reduced by using pedicle screw instrumentation. The sequence of surgery includes performing a laminotomy and facetectomy through a tube system, removing the disc and cartilage endplate, placing the intervertebral cage, placing the pedicle screws and rods, and reducing listhesis. Limitations of known cages include movement and distortion or bending of the cage during reduction of listhesis. This is predominantly due to the design of the cages, including the shape and surface geometry. It is known that movement of the cage may result in suboptimal position of the cage after reduction.

In practice, successful fusion depends on numerous factors, some of which relate to the cage. The larger the size of the cage the more bone graft material is contained in the cage thereby forming a larger and stronger bony fusion over time. The modulus of elasticity of the material from which the cage is manufactured should also be similar to that of vertebral bone to optimise load transfer between the cage and the adjacent vertebral bodies and reduce the effects of stress shielding on the graft material. Relative movement between the cage and the adjacent vertebrae has to be limited, which is currently mainly achieved by pedicle screw instrumentation, preferably avoided, until bony fusion has occurred.

A surgeon often experiences difficulties in and safety concerns around the placement of the cage. When placing a cage between the vertebrae there is significant risk of damaging radicular nerves in the foramen and lateral recess and the cauda equina, damaging the dural sac and causing a resultant CSF leak, damaging blood vessels anterior to the vertebral body namely the aorta, the inferior vena cava and/or the iliac vessels, and damaging the vertebral bony endplate.

Another problem with known cages is that of cage migration and movement. It has been found that a disadvantage of a number of known cages is that they do not sit securely between the vertebrae and, as a result, move or migrate in the postoperative period. This movement of the cage mainly occurs anteriorly or posteriorly. Posterior movement may lead to nerve and cauda equina compression, which may cause nerve damage and neurologic deficit. Any migration may, in turn, cause non-union of the fusion and possible failed surgery.

It is accordingly an object of the invention to provide an intervertebral fusion cage that will, at least partially, address the above disadvantages. It is also an object of the invention to provide instrumentation for and a method of inserting an intervertebral fusion cage that will, at least partially, address the above disadvantages.

It is further an object of the invention to provide an intervertebral fusion cage, instrumentation for and a method of inserting such cage which will be useful alternatives to existing intervertebral fusion cages, instrumentation used in inserting the cages and methods of inserting them.

SUMMARY OF THE INVENTION

According to the invention there is provided an intervertebral fusion cage for insertion between vertebrae, the cage including:
- a body defining a first, anterior portion, a second, posterior portion and a central portion extending between the anterior and posterior portions; wherein the central portion defines a first surface which is, in use, a top surface and a second surface which is, in use, a bottom surface, the top and bottom surfaces carry gripping formation for gripping end plates of the vertebrae; and
- wherein the gripping formations on the top and bottom surfaces face substantially opposite directions such that the gripping formations on the top surface obstructs movement in a first direction while the gripping formations on the bottom surface obstructs movement in a second direction, which is substantially opposite the first direction.

The gripping formations may be in the form of upstanding serrations located on the top and bottom surfaces respectively.

The gripping formations may be arranged as a series of parallel serrations.

The serrations are preferably spaced apart by intermediate, preferably substantially flat, sections located between adjacent serrations.

The serrations may extend across the width of the top and bottom surfaces respectively. Alternatively, the serrations may be arranged in discreet areas of the top and bottom surfaces, such as along the periphery of the top and bottom surfaces, for example.

In one embodiment one of the serrations located on the top surface of body faces in substantially the opposite direction than the other serrations located on the top surface for engaging the cortical rim of the vertebra.

The cage may further include an engagement formation for engaging vertebrae and thereby preferably also locating the cage relative to the vertebrae.

The engagement formation may be carried by the body, and in particular by the anterior portion. The engagement formation is preferably defined by the anterior portion and shaped for complemental engagement with the vertebrae, preferably with the anterior cortical rims of the vertebrae. The engagement formation may have concave upper and lower surface for complemental engagement with the cortical rims for the vertebrae located in use above and below the cage. Preferably, the concave upper and lower surfaces define channels in which the cortical rims of the upper and lower vertebrae are in use received.

The cage may include a pillar providing support between the vertebrae so as to prevent the cage from collapsing in use. The pillar may be defined by the anterior portion and preferably forms part of the engagement formation. In particular, the pillar is formed between the upper and lower concave surfaces of the engagement formation.

Preferably, the intervertebral fusion cage has a volume for receiving bone graft material. The volume for receiving bone graft material may be in the form of an internal cavity which is open to the top and/or bottom surfaces. The internal cavity may be open to the top and bottom surfaces such that it extends through the cage. The cage may further carry openings in its side walls extending between the anterior and posterior ends, the openings being in communication with the internal cavity such that, in use, the bone graft material inside the internal cavity may be in contact with bone graft material in the disc space by means of the openings.

The cage may be tapered, preferably from its anterior and to its posterior end. The taper angle may be between about 5° and about 20°, preferably between about 5° about 15°.

In accordance with a second aspect of the invention there is provided insertion instrumentation for inserting a fusion cage into a disc space, the insertion instrumentation including:
- a blade structure having a pair of blade members, each blade member having an anterior portion and a posterior portion, the ends of the blade members carried by the posterior portions being connected to one another while the ends of the blade members carried by the anterior portions are free to move relative to one another;
- a drive tool being movably connectable to the blade structure, the drive tool having a first, anterior end for driving the cage along an insertion direction towards the disc space and a second, posterior end carrying griping means for gripping and driving the drive tool; and
- an attachment tool for attachment to the cage, the attachment tool being removable attachable to the cage at a first, anterior end of the attachment tool;
- wherein the drive tool and attachment tool are movable relative to one another such that movement of the drive tool impart a force onto the cage driving it in the insertion direction.

The blade structure may include a body to which the posterior ends of the blade members are connected such that the blade members extend substantially perpendicularly from the body.

The body of the blade structure and drive tool preferably comprise complementary shaped engagement formations that are operable to allow relative movement between the blade structure and drive tool when the drive tool is moved to drive the cage in the insertion direction.

The drive tool may carry an external thread for engagement with a threaded socket carried by the body of the blade structure such that, in use, rotation of the drive member drives its anterior end imparting the driving force onto the cage in the insertion direction.

The insertion instrumentation may further include a thrust member locatable between the drive tool and the cage such that the force driving the cage is imparted on the thrust member, which in turn impacts the cage.

The insertion instrumentation may also include an adjustable stop for limiting the movement of the blade structure in the insertion direction. The adjustable stop may run on an external thread carried by the drive tool. Preferably, the adjustable stop includes a threaded collar running on the external thread carried by the drive tool.

The adjustable stop may carry projections for engaging an insertion tube used during the insertion of the cage and to facilitate turning thereof on the drive tool.

The elongate members may be in the form of thin, plate-like blades. In one embodiment the blades may have a thickness of between about 0.75 mm and 1.0 mm each or more than 1 mm.

Preferably, the edges of the blades at their anterior ends are rounded so as to prevent damage to the nerves and dura during the insertion of the cage.

In accordance with a third aspect of the invention there is provided a method of inserting the intervertebral fusion cage according to the first aspect of the invention into a disc space located between vertebrae of a patient, the method including the following steps:
  placing the cage between a pair of plates, preferably thin metal plates, particularly blades
  inserting the blades into the disc space between the vertebrae;
  advancing the cage between the metal plates in an insertion direction towards the disc space;
  positioning the cage between the vertebrae such that an engagement formation of the cage engages the anterior cortical rim of at least one of the vertebrae, thereby locating the cage relative to the vertebrae; and
  withdrawing the plates from the disc space.

The method may include the step of substantially preventing translational movement (both forward and backward) of the vertebrae relative to the cage and relative to each other by engaging the end plates of the vertebrae with the serrations located on the superior and inferior surfaces of the cage.

The step of advancing the cage between the metal plates may include sliding serrations of the cage on the smooth metal surface of the blades.

The step of advancing the cage between the metal plates may include the steps of:
  attaching an attachment tool to the cage;
  connecting a drive tool to a blade structure comprising the plates; and
  moving the drive tool relative to the blade structure to impart a driving force to the cage in order to drive it in the insertion direction;

The step of attaching the attachment tool to the cage may include threading an anterior end of the attachment tool an anterior or posterior wall of the cage.

The step of connecting the drive tool to the blade structure may include threading the drive tool through a threaded socket carried by the blade structure such that an anterior end of the drive tool extends through the socket.

The step of moving the drive tool relative to the blade structure may include rotating the drive tool to thread in further past the treaded socket into the blade structure. This step may include moving the drive tool about the attachment tool.

The method may further include limiting the movement of the blade structure in the insertion direction. This may include adjusting an adjustable stop until it impacts a posterior end of an insertion tube used in the insertion of the cage into the disc space.

The step of withdrawing the blades from the disc space may include moving the adjustable stop relative to the drive tool to remove the blades in a continuous and controlled manner.

The step of inserting bone graft material in the internal cavity of the cage may be carried out before inserting the cage between the vertebrae. Additional bone graft material may be inserted into the cage after placement of the cage in the disc space.

The method may include packing the remaining volume of the disc space with bone grant material before and after the cage is placed in position.

The method may include allowing contact between the bone graft material inside the cage and the bone graft material outside the cage through openings in the cage side walls.

The method may include widening a working corridor through which the disc space is entered so as to offer better vision into the disc space and allow it to be clean it out satisfactorily.

The step of widening the corridor may include the following steps:
  placing a tube on the facet and lamina;
  drilling the vertebral lamina and facet away and relieving any stenosis of the lateral recess, central canal and foramen;
  developing the disc space between the dura medially and the exiting nerve root in the foramen laterally;
  incising the annulus of the disc and flapping it upward and medially towards the dura;
  taking the flap up to the midline or across to the contralateral side, if possible;
  cutting the flap as broad as possible even if the disc space is narrow and collapsed; and
  placing a stay suture through the lateral margin of the flap and taking it outside the tube and attaching it to an artery forceps or similar tool which hangs free on the side of the patient performing mild continuous retraction of the dura and roots medially.

The method may include widening the disc space from top to bottom and from side to side to allow for the placement of a larger cage.

The method may further include the following steps:
  removing the overhanging posterior rim of the endplate of the vertebra above and below the disc space up to and across the midline, if possible; and
  loosening the annulus further across the midline for extra retraction on dural sac and space.

The method may, if listhesis is present, include placing pedicle screw instrumentation and reduction of listhesis or placing fixation screws in the cage.

BRIEF DESCRIPTION OF THE DRAWINGS

The invention will now be described in more detail, by way of example only, with reference to the accompanying drawings in which.

DESCRIPTION OF THE ILLUSTRATED EMBODIMENTS

Figure 1:
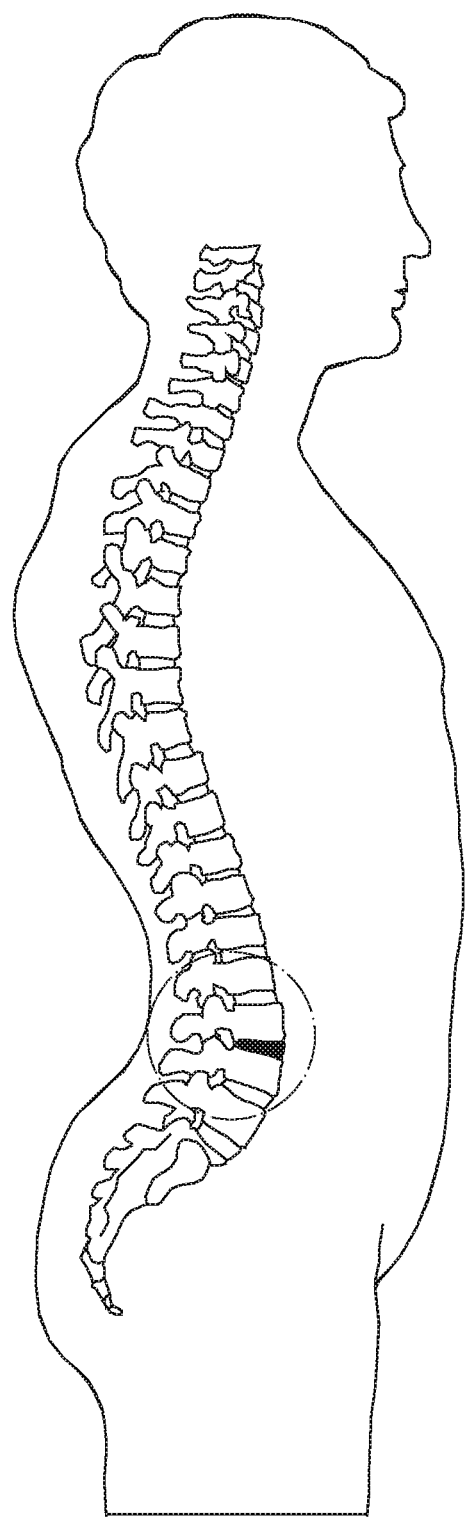
FIG. 1 shows a known intervertebral fusion cage located in use in the spine of a patient.
Figure 2A:
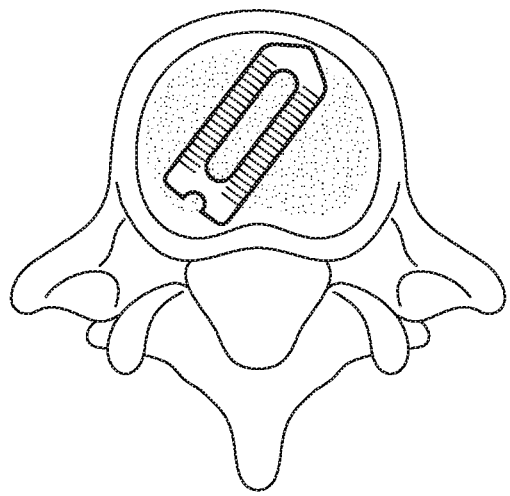
FIG. 2 shows a TLIF and PLIF type fusion cage in (a) and (b) respectively.
Figure 2B:
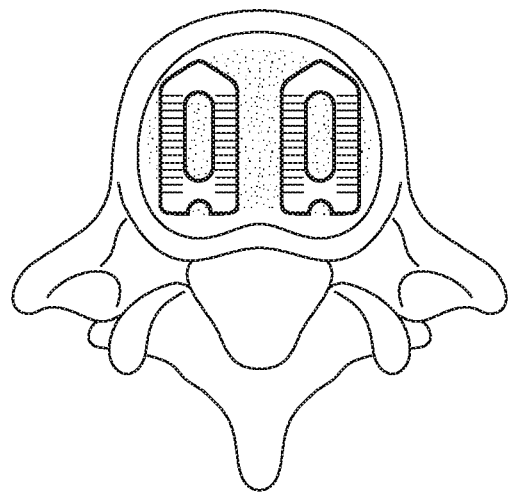
Figure 3:
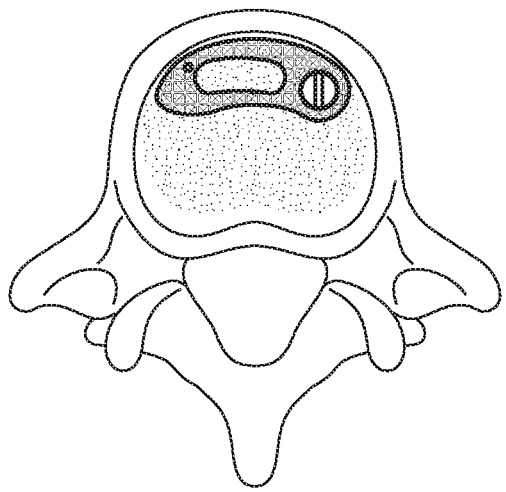
FIG. 3 shows a known crescent type fusion cage.
Figure 4:
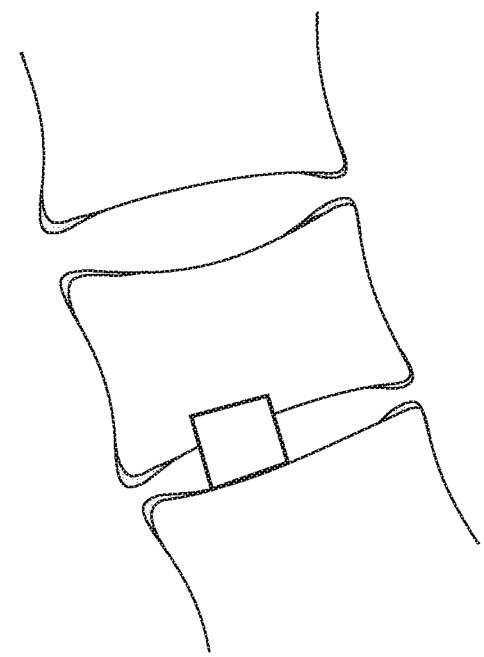
FIG. 4 shows subsidence of a known cage through the endplate of the vertebra above the cage.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "engaged" and variations thereof are used broadly and encompass both direct and indirect mountings, connections, supports, and engagements and are thus intended to include direct connections between two members without any other members interposed therebetween and indirect connections between members in which one or more other members are interposed therebetween. Further, "connected" and "attached" are not restricted to physical or mechanical connections. Additionally, directional indications such as "lower", "upper", "upward", "down" and "downward" designate directions in the drawings to which reference is made. The terminology includes the words specifically mentioned above, derivatives thereof, and words or similar import such as "anterior", "posterior", "superior" and "inferior". The words, "anterior", "posterior", "superior" and "inferior" are also synonymous with "front", "rear", "top" and "bottom" respectively, and may be used interchangeably. It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Referring to the drawings, in which like numerals indicate like features, a non-limiting example of an intervertebral fusion cage in accordance with the invention is generally indicated by reference numeral 10.

The intervertebral fusion cage 10 is suitable for insertion between vertebrae, particularly to fuse the vertebrae as part of a spinal fusion procedure (also referred to as spondylodesis or arthrodesis). It is envisaged that the fusion cage 10 would find particular application in the fusion of vertebrae in the lumbar spine but it is not limited to this application and could be used in the fusion of vertebrae in any of the cervical, thoracic and lumbar regions of the spine to prevent movement between the fused vertebrae. It is further envisaged that, with minor variations in design, the cage 10 could be used as an ALIF (anterior lumbar interbody fusion) cage or a LLIF (lateral lumbar interbody fusion) cage or a cervical cage. The invention would be particularly effective in the standalone ALIF cage by increasing the rigidity of the vertebra cage interface.

Figure 5:
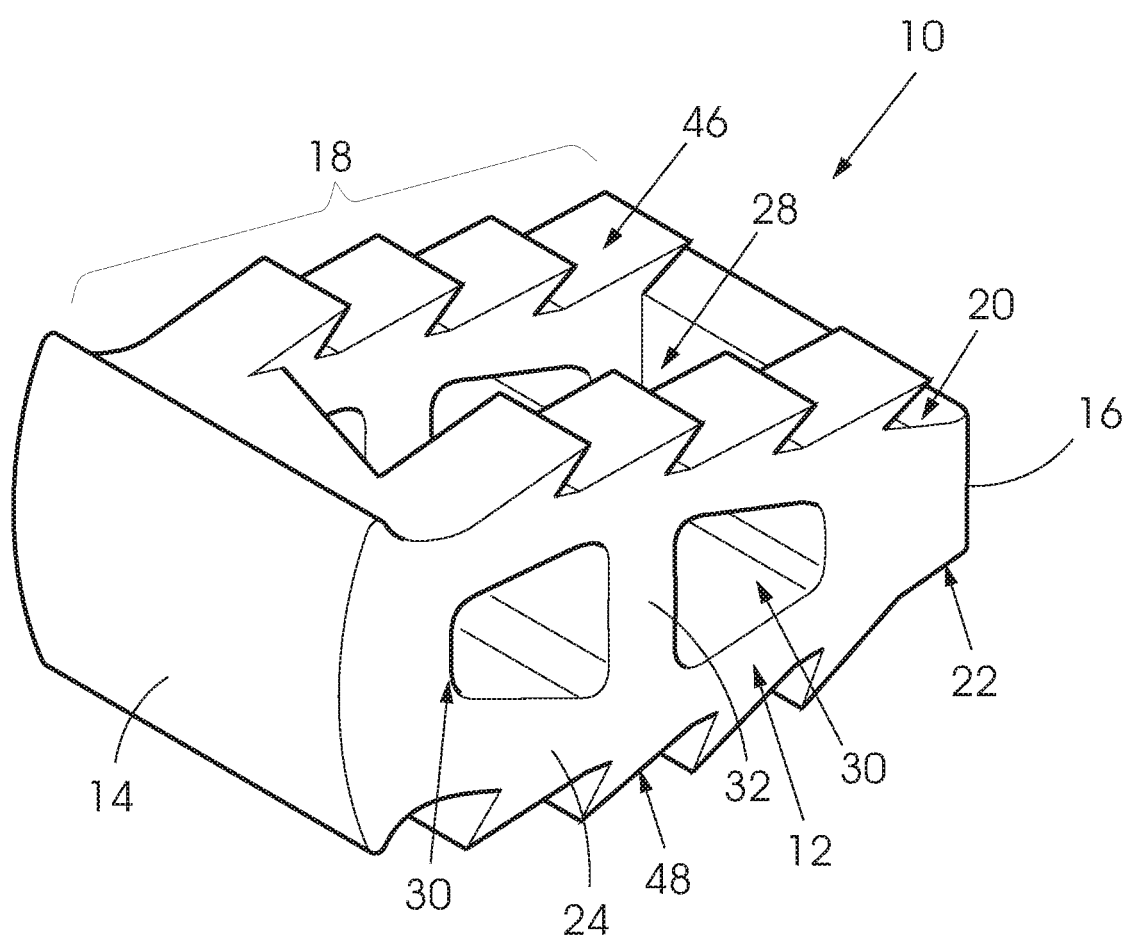
FIG. 5 shows a front perspective view of an intervertebral fusion cage in accordance with the invention.

Referring to FIG. 5, the fusion cage 10 has a body 12 defining a first end 14, which is in use an anterior or front end, and a second end 16, which is in use a posterior or rear end. A central portion 18 extends between the anterior 14 and posterior 16 ends. The body 12, and in particular the central portion 18, has a first surface 20, which is in use a top or superior surface, and a second surface 22, which is in use a bottom or inferior surface.

The body 12 is shaped complementally to the disc space between the two adjacent vertebrae in which the cage 10 is, in use, located. In other words, the cage 10 is shaped for complemental engagement with the endplates of the upper and lower vertebrae between which it is, in use, located.

Figure 6:
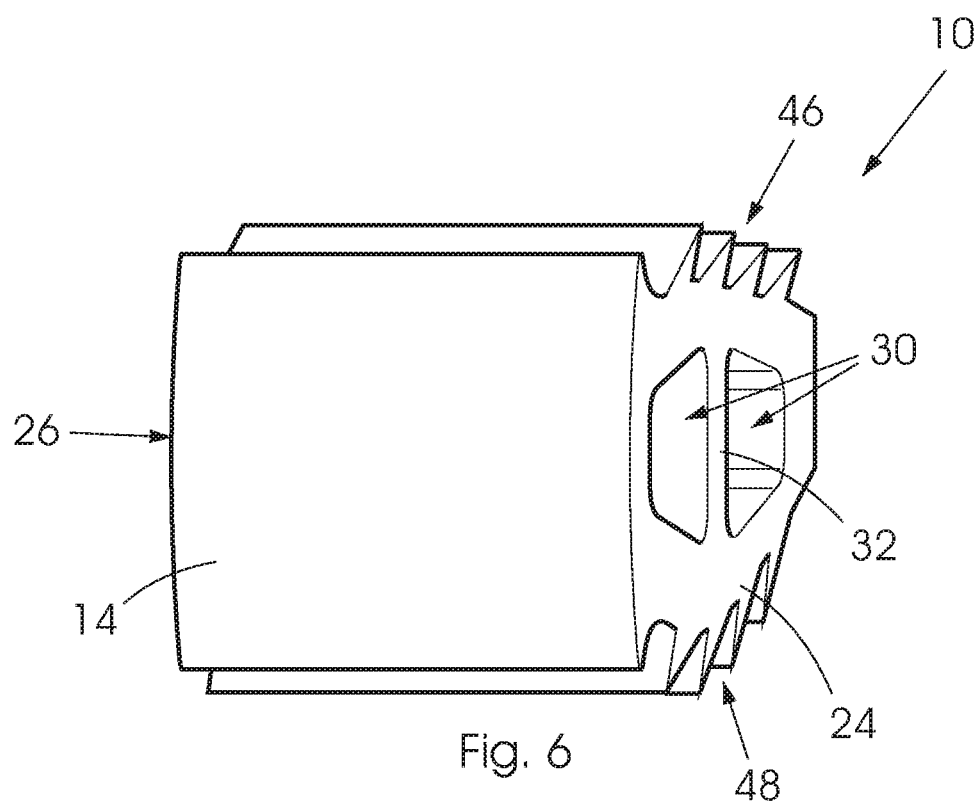
FIG. 6 shows a front view of the cage of FIG. 5.
Figure 7:
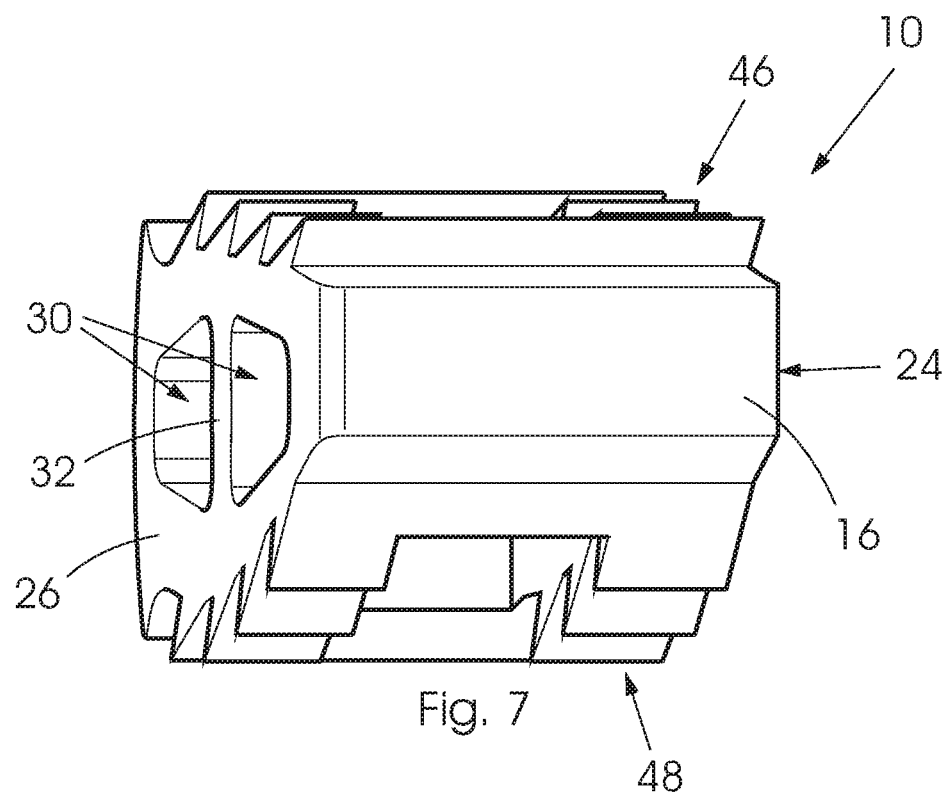
FIG. 7 shows a rear view of the cage of FIG. 5.
Figure 9:
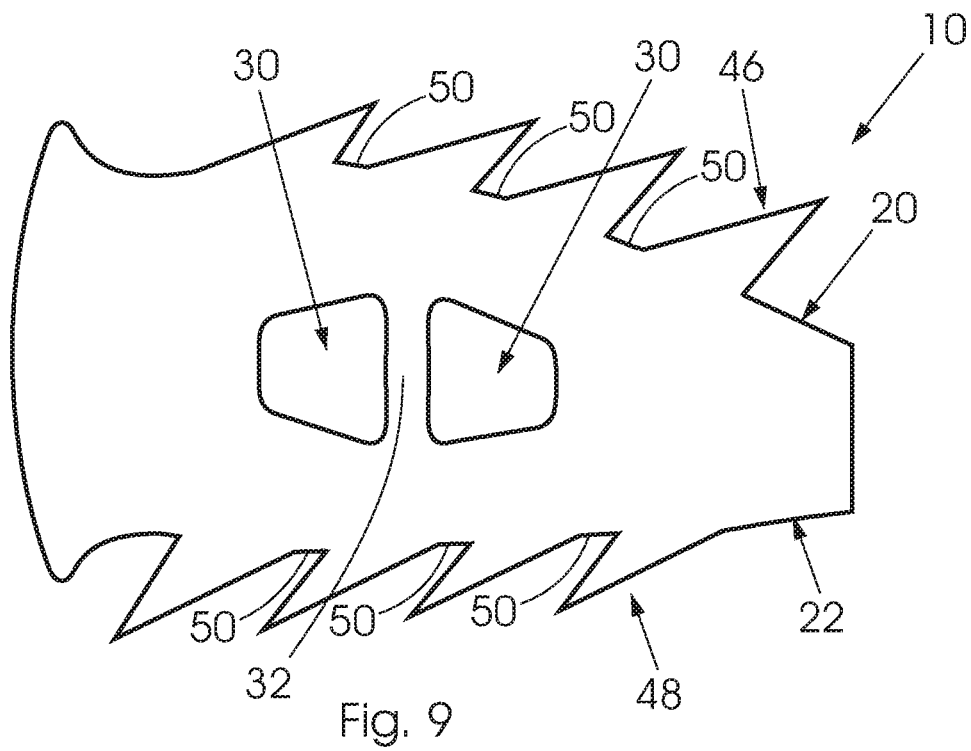
FIG. 9 shows a side view of the cage of FIG. 5.
Figure 10:
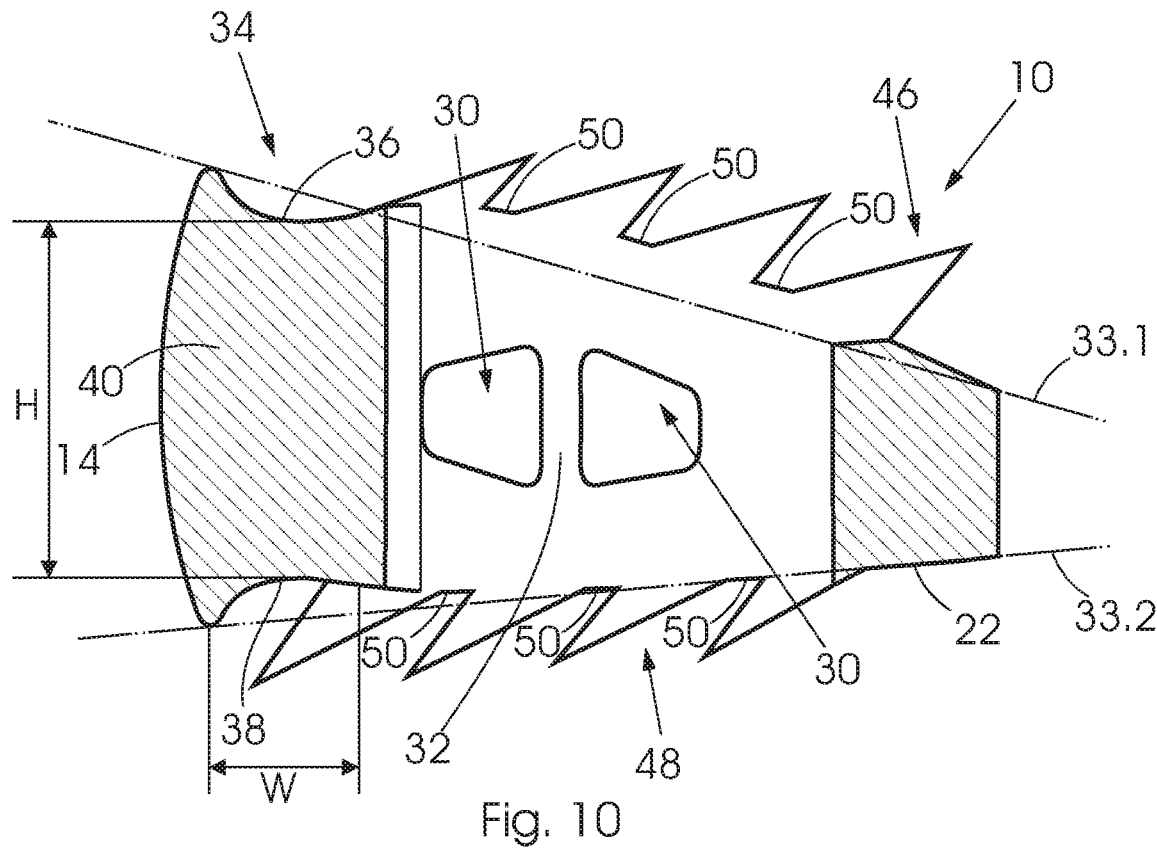
FIG. 10 shows a cross-sectional side view of the cage of FIG. 5.
Figure 11:
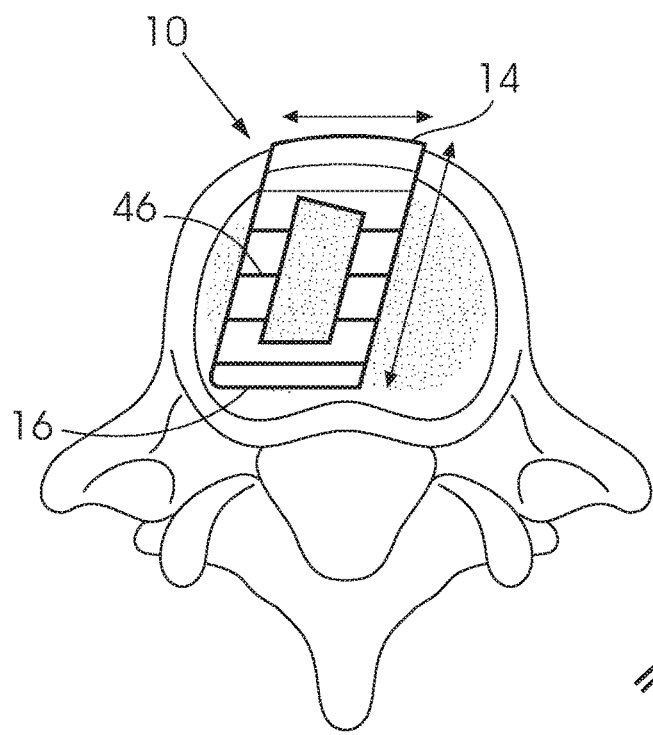
FIG. 11 shows a top view of the cage of FIG. 5 in use engaging the cortical rim of a vertebra.

The superior surface 20 of the body 12 substantially mirrors the concave shape of the upper vertebral endplate, i.e. the inferior surface of the upper vertebra against which the cage 10 in use rests. The degree of concavity of the upper vertebral endplate typically varies from anterior to posterior with greater concavity present at the anterior than posterior end of the vertebra. Accordingly, the superior surface 20 of the cage is generally convex with a greater degree of convexity in the region at the anterior end 14 than the region at the posterior end 16. Probably best seen in FIGS. 5, 9 and 10, the superior surface 20 is more convex towards its central and anterior regions and is flatter towards its posterior region. Referring now to FIGS. 6 and 7 it can be seen that the superior surface 20 is also convex from one side 24 to the other 26. The degree of convexity of the superior surface 20 is less across its width, i.e. from side to side, than across its length, i.e. from its anterior 14 to posterior 16 ends.

The degree of concavity of the upper vertebral endplate also varies between patients and, accordingly, the convexity of the superior surface 20 of the cage 10 may vary to accommodate different patients.

Similarly to the superior surface 20, the inferior surface 22 of the cage 10 substantially mirrors the concave shape of the lower vertebral endplate, i.e. the superior surface of the lower vertebra against which the cage 10 in use rests. The inferior surface 22 of the cage 10 mirrors the mild concavity of the superior endplate and, accordingly, is convex in shape across the length of the cage 10. The upper vertebral endplate of a patient is typically more concave than the lower vertebral endplate and the superior surface 20 of the cage 10 is therefore more convex than the inferior surface 22.

Figure 8:
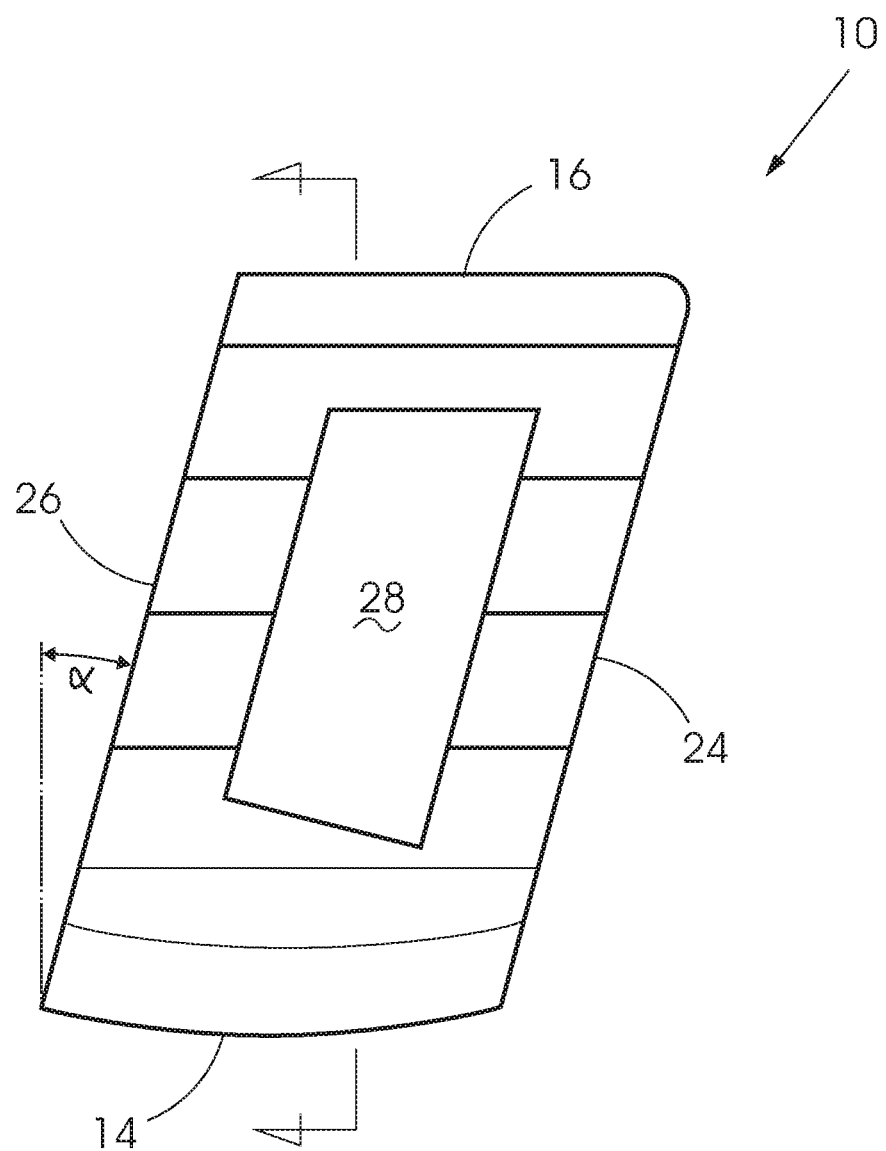
FIG. 8 shows a top view of the cage of FIG. 5.

The sides 24, 26 or lateral surfaces of the cage 10 are, in turn, substantially flat as shown in FIG. 8. It can be seen that the cage 10 is generally trapezoidal in shape. In this illustrated embodiment the cage 10 is generally in the shape of a parallelogram when view in plan (FIG. 8) with the lateral sides 24, 26 being angled at an angle α relative to the anterior 14 and posterior 16 ends. The angle α is typically between 20° and 30°.

Referring still to FIG. 8, it can be seen that the anterior end 14 is rounded, particularly convex, when viewed in plan. The convex anterior end 14 allows for complemental engagement to the posterior and inferior vertebrae. In other words, the anterior end 14 is shaped complementally to the periphery of the vertebrae. More about the engagement between the cage 10 and the vertebrae is said below.

The body 12 of the cage 10 further has a volume 28 for receiving bone graft material when inserting the cage in the disc space between the adjacent vertebrae. In the illustrated embodiment of the cage 10 the volume 28 for receiving bone graft material is in the form of an internal cavity. The cavity 28 is created by a cut-out extending through the central portion 18 of the body 12. The cavity 28 therefore extends through the superior 20 and inferior 22 surfaces of the body 12 such that the cavity is open to the top and bottom.

It is envisaged that the cavity 28 could be provided in a limited number of standardised sizes. For example, the cavity 28 could be provided in 3 or 4 different sizes for use on the complete spectrum of different cage 10 sizes. The use of standardised cavities would allow for standardisation of insertion instruments, which are described in detail below. It is envisaged that the minimum cavity height would be about 8 mm and the width of the cavity will be between about 10 mm and 14 mm. The cage width and, accordingly, the width of the cavity 28 depends in part on the lumber level where the fusion is carried out. The higher the lumber level the smaller the cage width and vice versa.

The body 12 further has windows or openings 30 located in the sides 24, 26 of the cage 10. The central cavity 28 is therefore open to the exterior of the cage 10 by means of the openings 30. A central pillar 32 dividing or located between the two openings 30 provides structural support, thereby improving the strength and, therefore, the load bearing capacity of the cage 10. The pillars 32 located in the lateral sides of the body 12 therefore prevent possible cage weakness and collapse under compressive loads when inserted in the disc space. It is envisaged that the pillars 32 could each have a width of between about 3 to about 5 mm. It should be understood that the size of openings 30 and of the pillar 32 can be varied to vary the resistance of the cage 10 to compressive forces. The size of the openings 30 and pillar 32 will also vary according to cage size.

In use, the bone graft material packed in the internal cavity 28 will make contact with the surrounding bone graft material placed around the cage 10 through the openings in the superior 20 and inferior 22 surfaces as well as the openings 30 in the lateral surfaces 24, 26. As a result, fusion will take place both inside and outside the cage 10 for the strongest possible union to occur.

The cage 10 is shaped to assist in the creation of lordosis of the spine when the cage is located in the spinal disc space between the vertebrae. The height of the cage 10 varies along its length with the maximum height being towards the anterior end 14, such that the cage 10 assists in creating the lordotic shape of the lumbar spine. In use, when located in the disc space, the apex of the convex superior surface 20 is located towards the middle of the vertebra, which substantially corresponds to the apex of the concave dome of the upper endplate above the cage 10. As mentioned above, the cage 10 tapers from the anterior end 14 down to the posterior end 16 as indicated by reference lines 33.1 and 33.2. The difference in height at the anterior 14 and posterior 16 ends depend on the lordosis or taper of the cage 10. The degree of lordosis required will be evaluated pre-operatively by measurement. It is envisaged that the taper angle (also referred to as the angle of lordosis of the cage 10) will be between about 5° and about 15°. In rare instances a taper angle of up to about 20° may be required. The taper angle could, for example, be varied incrementally to produce cages 10 having a taper angle of about 5°, 7.5°, 10°, 12.5° and 15°. The taper angle of the cage 10 may change after a period of patient use to determine optimal different degrees of lordosis required to treat the whole lumbar spine. In view of the above taper angles, it is envisaged that the maximum cage height will range from about 9 mm to about 18 mm.

From the above description of the cage 10 it should be understood that the cage 10 is shaped complementally to the vertebral end plates against which it rests when located in the disc space. In particular, the anterior end 14 is shaped to engage the vertebrae when the cage 10 is located in the disc space between the adjacent vertebrae. In particularly, the anterior end 14 defines an engaging formation 34 for engaging the vertebral body rim, preferably the anterior cortical rim, of at least one and preferably both of the vertebrae between which it is, in use, located. The engaging formation 34 defines a top or superior engagement surface 36 for engagement with the anterior cortical rim of the vertebra above the cage 10 and a bottom or inferior engagement surface 38 with the anterior cortical rim of the vertebra below the cage 10. Both the superior surface 36 and inferior surface 38 are concave in shape for complemental engagement with the rims. The superior concave surface 36 has a shorter radius than the inferior concave surface 38, thereby mirroring the curves of the bottom cortical ridge of the upper vertebra and the top cortical ridge of the lower vertebra respectively. Best seen in FIG. 10, at a point behind the concave curves of the superior 36 and inferior 38 surfaces both the superior and inferior surfaces transition into convex curves (which are described in detail above), which mirrors the concave surfaces of the cancellous part of the vertebrae. The concave curves of the surfaces 36 and 38 create a profile to engage the whole rim from anterior to posterior (or from lateral to medial in the case of a lateral cage). The concave surfaces 36 and 38 are respectively shaped to follow the slight radial or oval curvature of the cortical rims of the upper and lower vertebra.

Figure 12:
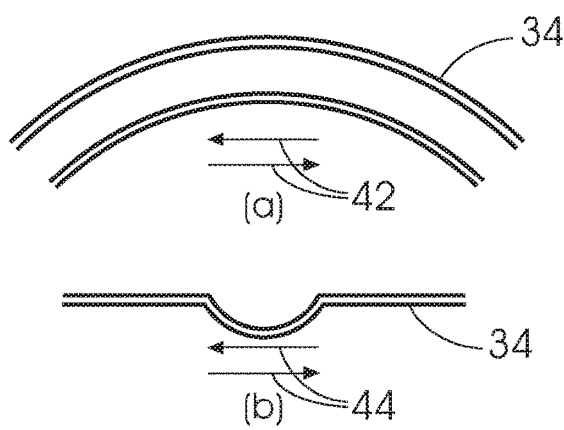
FIG. 12 shows schematic illustrations of the engagement between the cage of FIG. 5 and the cortical rim of the vertebra.

FIG. 12(a) shows a schematic top view of the engaging formation 34 engaging the convex cortical rim of bone of a vertebra. As a result of the curved shape across the width of the cage 10 and, accordingly the engaging formation 34, sideways movement in the directions 42 of the cage 10 is prevented. Similarly, FIG. 12(b) shows a schematic side view of the engaging formation 34 engaging the protruding cortical rim of bone of a vertebra. As a result of the upstanding ridge being received in the concave engaging formation 34, forwards and backwards movement in the directions 44 of the cage 10 is prevented. It should therefore be understood that the engagement formation 34 also act as a locating formation which, in use, locates the cage 10 on the vertebrae.

Returning to FIG. 10, the area of the cage 10 carrying the engaging formation 34 forms an anterior pillar or column 40 for supporting the vertebrae above and below the cage, in use. In the illustrated embodiment the pillar 40 is formed as a solid piece of material extending between the superior 36 and inferior 38 surfaces. However, it is envisaged that a different structural design could be used for the pillar 40 provided that sufficient resistance to compression is achieved. In use, when the cage 10 is located in the disc space between the vertebrae the cortical rim of bone of the vertebrae rests on either side of the pillar 40. The pillar 40 therefore needs to be of sufficient strength to prevent collapsing of the cage 10 and, accordingly, collapsing of the disc space.

The cage 10 and in particular the body 12 is preferably of unitary construction such that the pillar 40 is integrally formed with the side walls carrying the surfaces 24 and 26. As mentioned above, the side walls also provide structural strength to the cage 10 in order to prevent collapsing of the cage 10 in use. The anterior pillar 40 and side walls 24 and 26 form the structural backbone of the cage.

The superior 20 and inferior 22 surfaces carry gripping formations for gripping the vertebrae end plates when the cage 10 is, in use, located in the disc space. The gripping formations on the superior 20 and inferior 22 surfaces are indicated by the reference numerals 46 and 48 respectively. The gripping formations 46, 48 on the superior 20 and inferior 22 surfaces face substantially opposite directions such that the gripping formations 46 on the superior surface 20 obstruct movement in a first direction while the gripping formations 48 on the inferior surface 22 obstruct movement in a second direction. In use, the first and second directions are substantially opposite each other (i.e. 180° apart).

Figure 13:
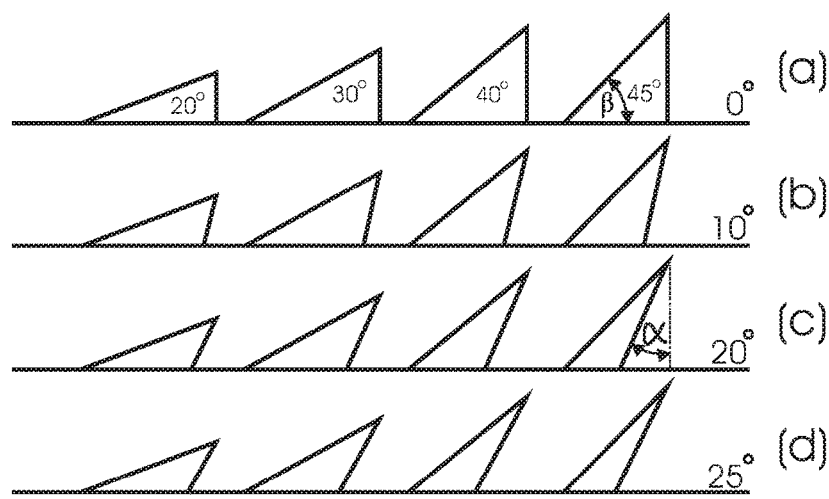
FIG. 13 shows a schematic illustration of different serration designs of the cage of FIG. 5.

In the illustrated embodiment the gripping formations 46, 48 are in the form of upstanding teeth or serrations extending from the superior 20 and inferior 22 surfaces respectively. The serrations 46, 48 are aggressive in that they are sized and shaped to grip into the endplates of the upper and lower vertebrae. The particular size and shape of the serrations 46, 48 may vary and a number of variations are illustrated in FIG. 13. FIG. 13 shows serration designs having an upslope angle β of between 20° and 45° and a downslope angle γ of between 0° and 20°. It is believed that a serration design having an upslope angle β of 30° and a downslope angle γ of 10° would be particularly useful in many fusion applications. It is envisaged that the serrations 46, 48 will have a height of about 2 mm, i.e. the serrations 46, 48 will project about 2 mm substantially vertically above the superior surface 20 of the cage 10. However, in some instances the serrations 46, 48 may have a height greater than 2 mm.

The serrations 46, 48 are arranged in substantially parallel rows across the superior 20 and inferior 22 surfaces in the central portion 18 of the body 12. The rows run transverse, preferably perpendicular, to the longitudinal centreline of the cage 10. i.e. the centreline running between the anterior 14 and posterior 16 ends of the cage 10. The rows of serrations 46, 48 are also spaced apart in that intermediate connecting sections 50 are located between adjacent rows. These intermediate connecting sections 50 provide substantially flat cage surface between the serrations 46, 48 upon which the endplates of the vertebrae may rest when the cage 10 is located in the disc space, thereby lowering the risk of subsidence through the endplates of the vertebrae. The intermediate connecting sections 50 therefore act as support surfaces for supporting the endplates of the vertebrae. The intermediate connecting sections 50 also assist the serrations 46, 48 in penetrating the endplates, thereby preventing movement of the cage 10 relative to the vertebrae. It should be understood that the intermediate connecting sections 50 aim to prevent the cage 10 from damaging the endplates to such a degree that subsidence may occur or shearing of the serrations 46, 48 through the bone.

It is envisaged that the length of each intermediate connecting section 50 could about 2 to 3 mm in length.

In the illustrated embodiment of the cage 10, the serrations 46, 48 run along substantially the entire length of the side pillars, i.e. the side walls of the cage carrying the surfaces 24 and 26 respectively. On the superior surface 20 the serrations 46 project backwards or posteriorly and on the inferior 22 surface the serrations 48 project forwards or anteriorly. The upward slope angle β on the convex part of the cage 10 will follow a 30° angle relative to a tangent line touching the point of origin at the base of the serration.

Figure 14:
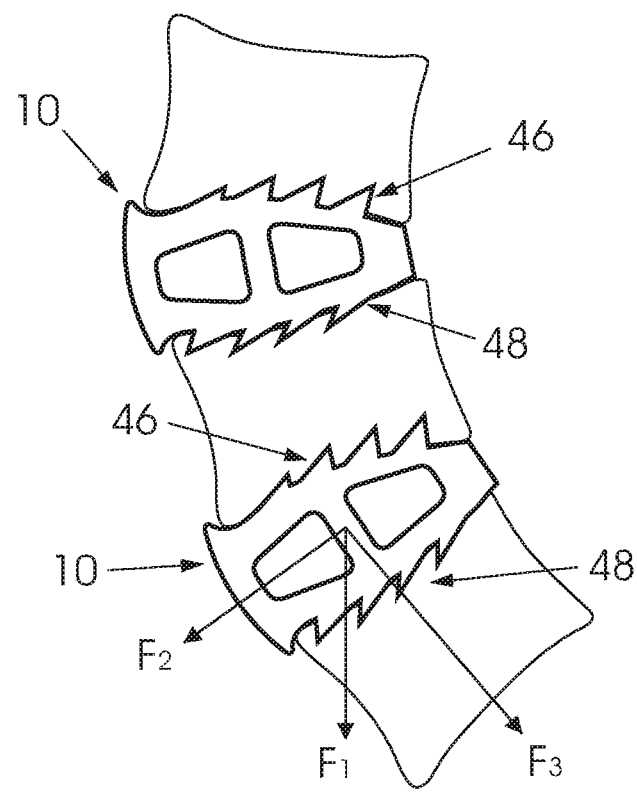
FIG. 14 shows a side view of two cages of FIG. 5 in use located between vertebrae of a patient.

From the above description of the serrations 46, 48 it should be understood that the cage 10 carries larger, more aggressive serrations in comparison to the knurling of known cages. If is believed that the design of the serrations 46, 48 of the cage 10 of the present invention allows for superior and stronger traction to the bone of the endplates of the vertebrae. In contrast to the known cages that the serrations 46, 48 of the cage 10 of the present invention acts as securing formations for securing the cage 10 in place between the vertebrae. The cage 10 is shown in FIG. 14 located in the disc space between the vertebrae.

Figure 15:
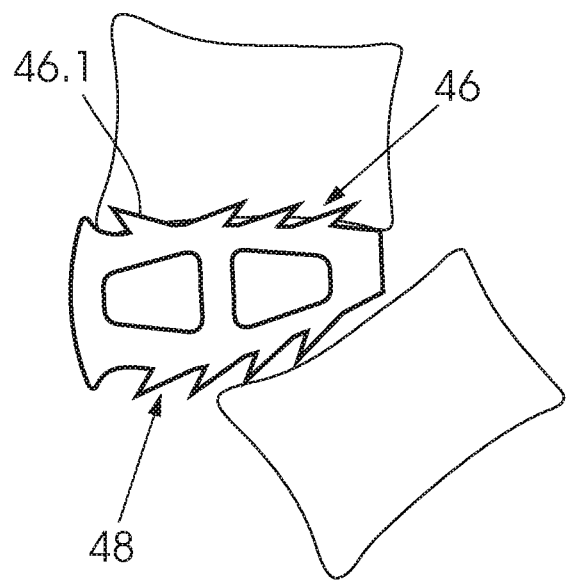
FIG. 15 shows a side view of the cage of FIG. 5 during insertion between two vertebrae.
Figure 18:
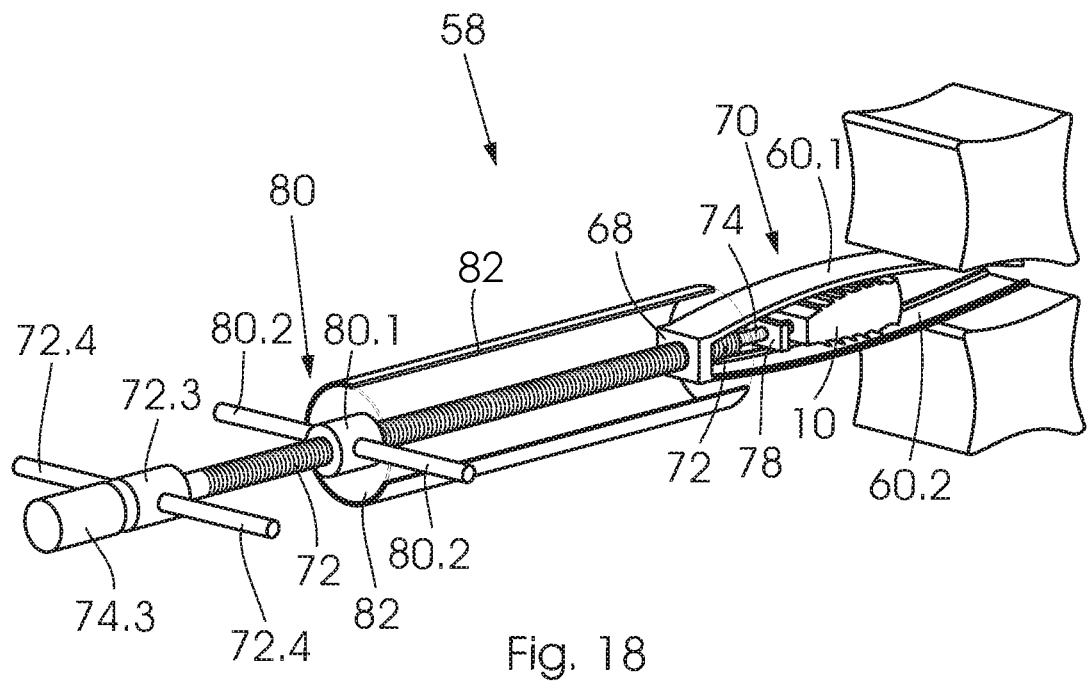
FIG. 18 shows a rear perspective view of the insertion instrumentation of FIG. 17.

It is envisaged that, in an alternative embodiment of the cage 10, the first serration on the superior surface 20 could be facing in a different direction than the rest of the serrations on the superior surface 20. An example of such an embodiment is shown in FIG. 15, in which the first serration 46.1 pm the superior surface 20 faces forwards while the rest of the serrations 46 face backwards. The forward facing serration 46.1 aims to ensure that the cage 10 moves with the upper vertebra during reduction of listhesis. As shown in FIG. 18 the first serration 46.1 engages the bone at the cortical rim of the upper vertebra.

It is further envisaged that in an alternative embodiment not illustrated in the accompanying drawings, the serrations 46, 48 may be arranged in discreet areas of the superior 20 and inferior 22 surfaces.

The cage 10 is preferably made from PEEK (Polyether ether ketone) as its modulus of elasticity resembles that of bone closely. This prevents stress shielding of the bone graft by the cage thereby stimulating the bone to grow and to react to loading stresses between the vertebrae by forming a stronger scaffold as would be the case with metal implants. However, it is envisaged that other materials, such as titanium either solid or as an intricate type of hollow matrix scaffolding, could be used. It is also envisaged that PEEK could be used with a layer of titanium plasma sprayed onto PEEK surface. It is believed that the PEEK covered with a titanium plasma layer could be particularly beneficial for the anterior pillar 40, and in particular its concave surfaces, as it could possibly stimulate better bone growth of the anterior cortical ridge surface onto the titanium plasma layer surface. It is yet further envisaged that titanium could be replaced by tantalum considering that both titanium and tantalum allow bone to grow onto their surface with a strong bond forming between the cage 10 and the bone.

It should be understood that the dimensions of the cage 10, and in particular the dimensions of the anterior column part 40 of the cage, will vary between patients. The dimensions of the cage 10 will typically be determined through approximation based on a MRI scan. It has been found that the width of the anterior cortical ridge as measured on vertebral bony specimens range from about 5 mm to about 10 mm. Accordingly, the width W of the concave section of the pillar 40 will be marginally wider than the width of the cortical rim, preferably by about 1 mm to about 2 mm. Ideally, the concave section of the pillar 40 will overlap the cortical ridge both posteriorly and anteriorly by about 1 mm to about 2 mm. It follows that the width W of the pillar is about 6 mm to about 12 mm. The length L of the concave section or channel from side wall 26 to side wall 28 will typically vary with the broadness of the cage between about 12 mm to about 20 mm. The height H of the anterior column 40 will typically range from about 10 mm to about 18 mm and more, if required. The height H is measured from the bottom of top concavity 36 to the top of the bottom concavity 38 and, accordingly, represents the minimum height of the anterior pillar 40.

Although not illustrated in the accompanying drawings the cage 10 according to the invention carries markers used to visualise the position of the cage in X-ray fluoroscopy and to position the cage correctly. The markers may be in the form of small rod like markers, preferably made from tantalum. The markers are located at the midpoint of the cage 10 vertically from top to bottom, at the midpoint distance measured from side to side, and about 1 mm to about 2 mm behind that anterior end 14 of the cage 10. The marker is typically 1 mm in diameter and the length will vary according to cage size but will be from the superior to inferior surface of the cage level with each surface. This anterior marker will in use aid in placing the cage 10 in the centre of the vertebra when viewed in plan and in determining the correct anterior position of the cage 10 with the anterior gutters 36, 38 resting on the cortical rims of the vertebrae above and below. Similar markers are located in the posterior corner regions of the cage 10 overlapping one another when viewed from the side and the cage being position at an angle of between about 20° to 30° from the midline. The posterior markers are typically about 2 mm from the posterior and side walls of the cage 10. The posterior markers in use indicate the position of the posterior wall of the cage and the correct angulation of the cage if they overlap closely. These markers will run from level with the superior to level the inferior surface in a vertical direction.

Figure 16:
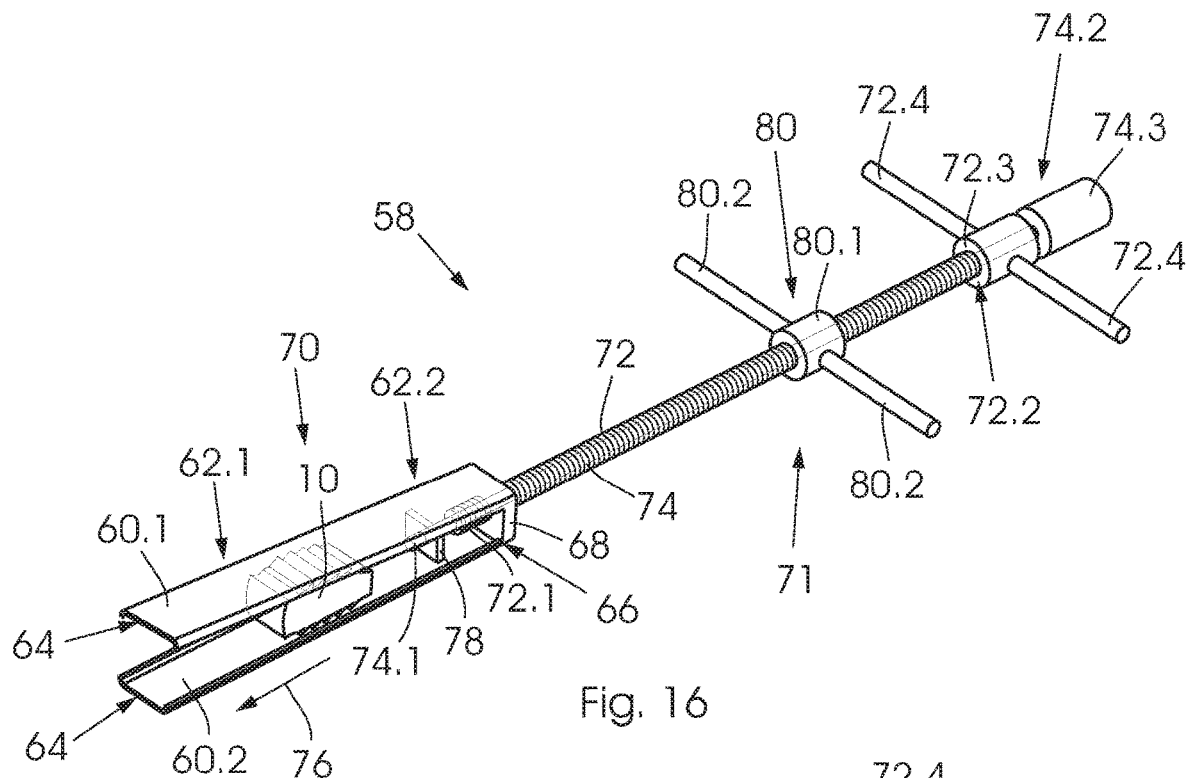
FIG. 16 shows a front perspective view of insertion instrumentation in accordance with the invention which are in use being used to insert the cage of FIG. 5 between two vertebrae.
Figure 17:
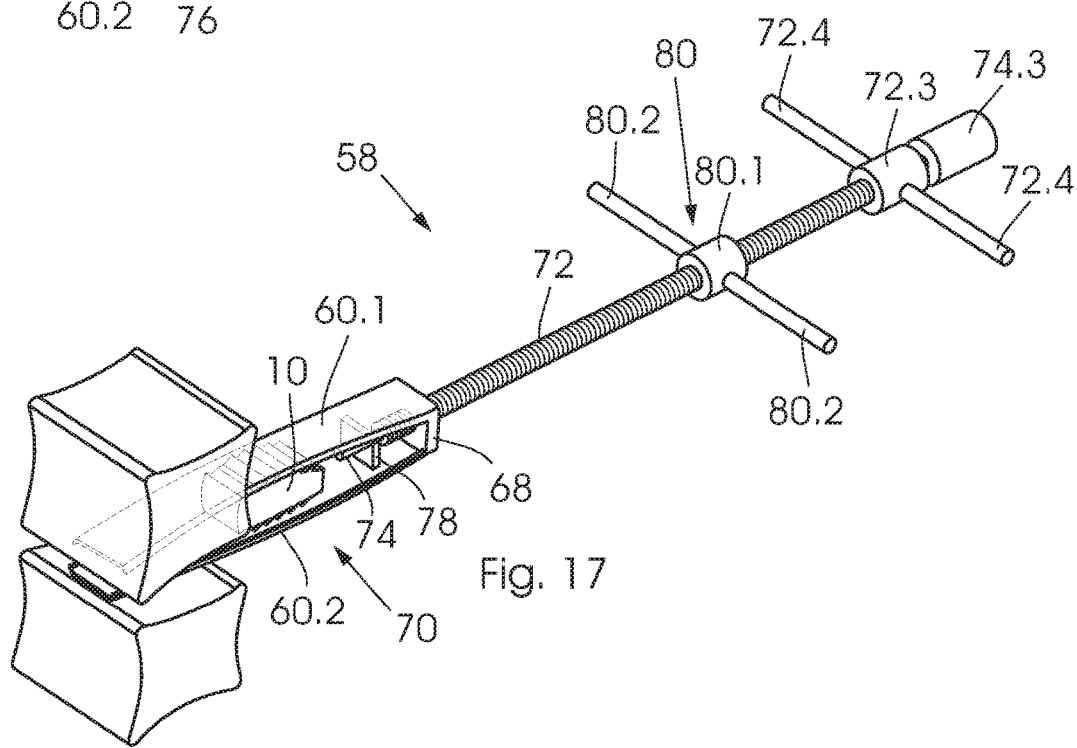
FIG. 17 shows a front perspective view of the insertion instrumentation of FIG. 17 in use.
Figure 19:
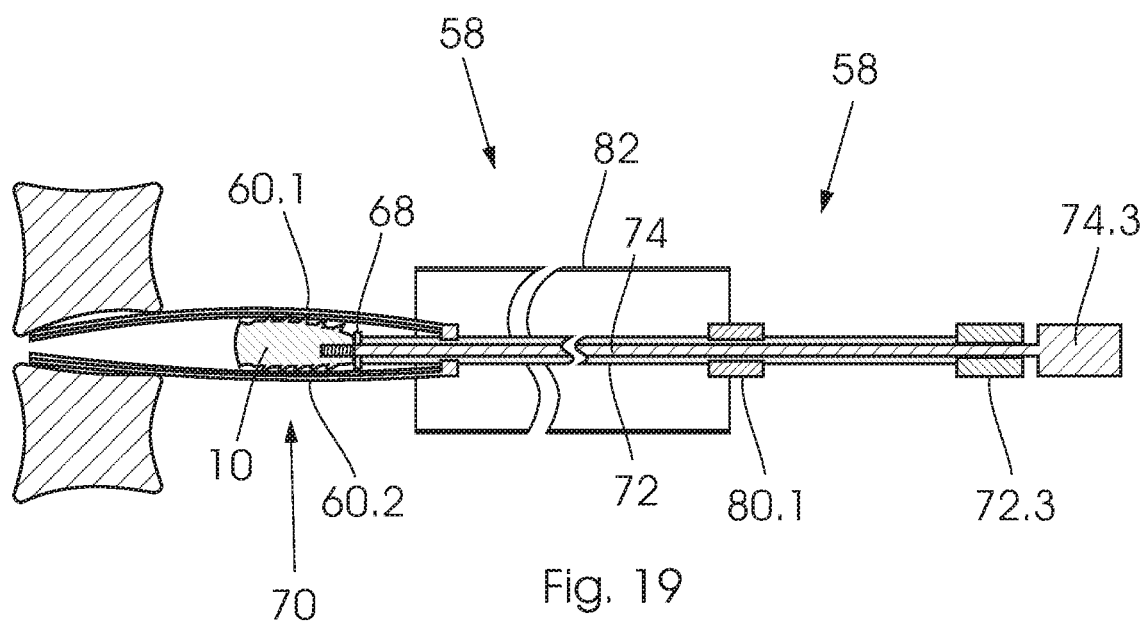
FIG. 19 shows a cross-sectional side view of the insertion instrumentation of FIG. 17.

As a result of the new design of the cage 10, and in particular due to the larger anterior pillar 40, the aggressive serrations 46, 48, the serrations 48 on the inferior surface of the cage projecting forward, its blunt nose at its anterior end 14 and the superior height of the engagement formation 34, a new set of instruments and a new method of inserting the cage 10 are required. Known instruments and methods of inserting cages posterior between the vertebrae will cause the serrations 48 to engage the vertebral endplate or posterior rim of the vertebral body. It will be impossible to advance the cage 10 forward using known instruments and methods without significant force, which could lead to destruction of the cage and/or the vertebral body, endplate or other soft structures like nerve roots. The insertion instrumentation according to the invention will now be described with reference to FIGS. 16 to 19, in which the instrumentation is indicated by reference numeral 58. FIG. 16 shows the instrumentation while FIGS. 17 to 19 show a schematic representation of the instrumentation in use during a cage fusion using minimal invasive TLIF performed through an insertion tube 82. The insertion tube 82 impacts anteriorly onto the posterior border of the facet joints of the vertebrae of the patient. The tube 82 is attached outside the patient with a rigid arm to the operating table. It is thus a fixed structure (immovable to a great degree although its position may be changed by loosening and the tightening the arm structure).

The instrumentation 58 includes a pair of insertion members in the form of thin plates or blades 60.1 and 60.2 for inserting the cage 10 into the disc space between the vertebrae. The blades 60.1, 60.2 are elongate and in the form of thin metal strips, preferable having a thickness of between about 0.75 mm and 1.25 mm, for example about 1 mm. The blades 60.1, 60.2 need to be rigid and strong enough to perform distraction of the vertebrae without bending excessively but thin enough to bend for cage positioning between the vertebrae and not adding to much height to the cage insertion instrument construct.

The posterior ends 66 are connected to a body 68, which is illustrated as an end plate, such that the blades 60.1, 60.2 extend from the end plate. Together the end plate 68 and blades 60.1, 60.2 form a blade structure 70. In use, the complete blade structure 70 resides inside the patient. The size of the blade structure 70 may therefore vary according to cage size used.

The anterior ends 64 of the blades 60.1, 60.2 are shaped to prevent damage to the nerve roots and dura during the insertion of the cage 10. In particular, the edges of the anterior ends 64 are rounded. It is envisaged that the blades 60.1, 60.2 could be curved over their longitudinal length to allow easy insertion of the anterior margins into the disc space. However, the blades 60.1, 60.2 may also be straight. In the preferred embodiment, the margin (also referred to as edge) of the anterior end 64 of the blades 60.1, 60.2 is slightly curved from side to side (medial to lateral) and the edges are rounded. The side margins of the top 60.1 and bottom 60.2 blades are curved downwards and upwards respectively to perform gentle retraction on the dura and nerve roots medially and the exiting nerve root laterally. The margin of the anterior end 64 of the blades 60.1, 60.2 are curved to prevent damage of anterior structures or the vertebral endplate. All the edges of the blades are rounded.

The length of the blades 60.1, 60.2 may typically vary between about 60 mm to about 140 mm, depending on the size of the cage 10 to be used and size of the specific patient. The width of the blades 60.1, 60.2 may typically vary between about 10 mm and 20 mm in TLIF type cages and between about 30 mm and 50 mm in ALIF type cages. Again, the width and length of the blades will typically be narrower in cervical cages. The distance between the blades 60.1, 60.2, measured at the longitudinal centre line, is typically between about 10 mm and 20 mm. The blade measures provided above are typical ranges and it is envisaged that in some instances blades of alternative sized may be used. A set of insertion instrumentation 58 will typically include blades 60.1, 60.2 of various sizes to choose from during the surgery depending on external factors, such as patient size and anatomy.

The blades 60.1, 60.2 used in ALIF cage placement, and in particular cervical cage placement, could include protrusions thereon to prevent inadvertent movement into the spinal canal with damage of the spinal cord in the cervical spine and damage of the cauda equina in the lumbar spine. The surface, which is in use the upper surface, of the top blade 60.1 and the surface which is in use the lower surface of the bottom blade 60.2 could each carry a protrusion such that the protrusions extend in substantially opposite directions outwardly. The protrusions typically extend perpendicularly from the centre of the blades 60.1, 60.2. The blades used in ALIF cage placement typically have protrusions about 35 mm to 45 mm from the edge of their anterior end 64. The blades used in cervical cage placement typically have protrusions about 12 to 20 mm from the edge of their anterior end 64, depending on patient size. The length of the protrusions is about 5 mm. The protrusions are typically cylindrical or pin-shaped and terminates in a rounded or dome-shaped end. It is envisaged that the diameter of the protrusion may be about 2 mm. Although not excluded from the scope of the invention, it is unlikely that that the blades used for TLIF cage placement will require protrusions due to the anchoring of a stop 80 against the insertion tube 82. More about this is said below.

In order to advance the cage 10 along the blades 60.1 and 60.2 a drive mechanism 71 is used. In use, the drive mechanism engages the cage 10 and drives it along the blade structure 70 in order to insert it into the disc space.

The drive mechanism includes a drive tool in the form of a first elongate member 72, typically in the form of a cylinder. An anterior end portion 72.1 is shaped to engage the end plate 68 while it posterior portion 72.2 carries a removable head 72.3. The head 72.3 is fixed in position using locking nuts or, alternatively by screwing it onto a short threaded section in discontinuation with the full length thread of the cylinder to effect a stop at the same level as the edge of the posterior end 72.2. The head 72.3 further carries handles 72.4. The handles 72.4 facilitate gripping of the cylinder 72 and provides mechanical leverage in order to facilitate rotation of the cylinder in use. The cylinder 72 carries an external thread running along at least a major portion thereof. The cylinder 72 typically has an outer diameter of about 8 mm and an internal diameter of about 4.5 mm. The internal bore runs along the entire length of the cylinder 72 to allow an attachment tool in the form of a second elongate member, typically in the form of a rod 74, to be received therein. The internal bore of the cylinder 72 is open at both ends such that the rod 74 is allowed to pass through the cylinder. The rod 74 has an anterior end portion 74.1, which is shaped to engage the cage 10, and a posterior end portion 74.2, which terminates at an enlarged head 74.3.

The enlarged head 74.3 facilitates easier screwing of the rod 74 into the cage 10 and acts as a stop against the posterior end 72.2 of the cylinder 72. The rod 74 carries an external thread running along at least of portion of its length. The anterior end 74.1 of the rod 74 and the cage 10 carry complementary shaped engagement formations such that they are removable engageable with one another. In the illustrated embodiment the external thread of the rod 74 engages an internally threaded bore 75 in the cage 10. The diameter of the rod 74 is about 4 mm, such that it is allowed to slide unobstructed along the internal bore of the cylinder 72. The enlarged head 74.3 on the rod 74 and the head 72.3 on the cylinder act to limit the relative movement between the rod and cylinder. In use, when the anterior end 74.1 of the rod 74 is engaged to the cage 10 the cylinder 72 is movable about the rod so as to drive the cage 10 in the direction 76, i.e. towards the patient in use. The forward movement of the cylinder 72 is achieved through rotation of the handles 72.4, which threads the cylinder through the threaded opening in the end plate 68.

In the view of the above, the cylinder 72 is also referred to a drive tool or insertion tool. It should further by understood that the function of the rod 74 is to attach the cage 10 to the insertion tool 72. Accordingly, the rod 74 is also referred to as an attachment tool for attachment to the cage 10. The length of the rod 74 is typically between about 250 mm and 300 mm for placement of an TLIF type cage. The length of the insertion tool 72 is shorter than the rod 74.

A thrust member 78 may be included between the anterior end 72.1 of the cylinder 72 and the cage 10 so as to increase the surface area acting on the cage 10 when driving it along the blades 60.1, 60.2. The thrust member 78 typically has an internally threaded bore corresponding to the thread diameter of the rod 74. In use, the rod 74 extends through the thrust member 78 such that the cylinder 72 impacts on the thrust member, which, in turn, impacts on the cage 10. The force being exerted by the cylinder 72 during advancement of the cate 10 will impact on the posterior and side walls of the cage, thereby allowing a much greater insertion force. The greater force will more likely result in successful placement of a sufficiently large cage 10. The allowable distraction force on the metal blades 60.1, 60.2 is also greater without cage failure occurring. A further advantage of the use of the thirst member 78 is that it reduces the risk of cage breakage during insertion because of spreading the insertion force over a wider area.

The instrumentation further includes an adjustable stop or obstructing formation 80. The stop 80 in use limits the movement of the blade structure 70 and cylinder 72 (unless the cylinder is being turned) in the direction 76 toward the patient. The stop 80 has a collar 80.1 that is threaded to run on the external thread of the cylinder 72. The collar 80.1 is typically about 20 mm in length. Handles 80.2, which are preferably fixed, are attached to the collar 80.1 to facilitate turning of the collar, when required. The handles 80.2 project substantially perpendicularly from the collar 80.1 such that, in use, they rest against the posterior end of the insertion tube 82, thereby preventing forward movement of the cylinder 72 and, accordingly, the blades 60.1, 60.2.

FIGS. 17 to 19 show a schematic representation of the instrumentation in use during a cage fusion using minimal invasive TLIF performed through the insertion tube 82.

A skilled person will appreciate that the cage 10 will be made available in various sizes to accommodate different patients. However, it is envisaged that the width of the cages 10 will vary from about 10 mm to about 20 mm. the depth of the cages 10 will range from about 30 mm to about 45 mm.

The method of inserting the intervertebral fusion cage 10 between vertebrae of a patient will now be described. The method includes performing disc space decompression and removal, and allows for a wider and/or higher cage 10 to be placed in the disc space between the vertebrae. The method includes the step of determining the length of the cage 10. This typically includes measuring the pre-operative MRI scan obliquely from posterior vertebral body rim to about 1 mm to 2 mm past the anterior vertebral body rim. The height of the cage 10 (typically ranging from about 8 mm to about 16 mm and more) is determined with pre-op measurements on X-ray photos and/or MRI scan(s). The final cage height is determined during the operation by using different size trials and by evaluating the height and lordosis correction with intra operative Fluoroscopy, for example by using a portable X-ray machine.

The method described is a minimal invasive TLIF procedure and includes placing a tube 82 on the facet and lamina from one side. The vertebral lamina and facet is then drilled away and any stenosis of the lateral recess, central canal and foramen is relieved. The posterior surface of the disc is then exposed and the disc space is developed between the dura medially and the exiting nerve root in the foramen laterally. The method includes incising the annulus of the disc and flap or fold this upward and medially towards the dura. This flap is taken up to the midline or across to the contralateral side if possible. The flap is cut as broad as possible even if the disc space is narrow and collapsed. A small stay suture is placed through the lateral margin of the flap, taken outside the tube and attached to an artery forceps or similar tool which hangs free on the side of the patient performing mild continuous retraction of the dura and roots medially. The purpose of the flap is to retract the dura medially. An advantage of this technique is that a wider space or working corridor to enter the disc, remove it and eventually place the cage 10 is created. The wider working corridor offers better vision into the disc space to clean it out satisfactorily. The use of an operative microscope throughout the procedure affords excellent vision. Another advantage is that flap also protects the dura and nerve roots from harm or injury during surgery in the disc space. This technique further provides soft retraction to the nerves which may otherwise be damaged by mechanical retraction and it frees up a hand of the surgeon which may be required to perform manual retraction from time to time.

The method of the invention further includes removing the posterior rim of the endplate of the vertebra above and below the disc space up to and across the midline, if possible. The purpose of this step is to widen the disc space from top to bottom and from side to side to allow for the placement of a larger cage 10, in height and width, in the disc space. This step further loosens the annulus even more for extra retraction and room. The wider cage 10 provides a larger area of support between the vertebrae with less risk of cage subsidence. As a result of the increased disc space in which the cage 10 is received this step further allows a longer cage to be used and, accordingly, a greater total length of serrations on the superior 20 and inferior 22 surfaces of the cage 10. This in turn increases the grip of the cage 10 on bone for better resistance of translation (both forward and backward) movement of vertebra relative to the cage and relative to each other. The improved resistance to movement better maintains reduction of the listhesis, if present. The wider cage 10 further allows for a larger central cavity 28 for increased and superior bone area contact to the vertebra and, therefore, an increased likelihood of better fusion.

After opening and cleaning the disc space the next step is to insert the cage 10 therein. This is achieved using the instrumentation 58 described above. The cage 10 is placed between the metal blades 60.1, 60.2 outside the patient. The two blades 60.1, 60.2 are inserted between the vertebrae in the cleaned out disc space. The anterior ends 64 of the blades are inserted into the disc space such that edges of the anterior ends 64 of the blades are positioned on the cortical bony edge of the vertebrae or just behind it. The optimal position will be determined in use. The step of placing the blades 60.1, 60.2 between the vertebrae will typically include front margins of the blades between the vertebrae the opposing blades will have to be pushed towards each other to achieve entry into the disc space. A pincet or forceps like tool will achieve this initially. Thereafter it will be pushed forward in the disc space by the insertion tool.

With the blades 60.1, 60.2 located between two opposing vertebrae in the disc space at the correct and required depth, the stop 80 is adjusted so that locates against the posterior end of the insertion tube 82. In this resting position against the insertion tube 82, the stop 80 prevents forward plunging of the blades 60.1, 60.2 between the vertebrae, thereby preventing accidental damage to vital structures anterior to the vertebrae, such as the aorta and/or vena cava, which could be fatal.

With the blades 60.1, 60.2 in the disc space the cage 10 is advanced along the longitudinal lengths of the blades 60.1, 60.2 and into the disc space until the required position is achieved. The step of positioning the cage 10 in the disc space between the vertebrae includes locating the cage using the engaging formation 34. In particular, the cage 10 is located by engaging the anterior cortical rim of at least one of the vertebrae with the engaging formation 34. As the cage 10 is advanced forward the blades 60.1, 60.2 will perform distraction of the disc space, which will allow entry of the cage prosthesis between the vertebrae into the disc space. The serrations and in particular the forward facing serrations 48 located on the inferior surface 22 are allowed to move, particularly slide, unobstructed along the smooth metal surface of the blades and into position. Once the cage 10 is in position the insertion instrumentation 58, and in particular the rod 74, is disconnected from the cage 10 and the metal blades are withdrawn from the disc space by removing them backwards in a controlled continuous motion. The optimal resting position of the front edge or margin of the blades 60.1, 60.2 will be determined during use but will most likely be at the junction of the cancellous endplate and cortical rim or on the cortical rim itself to prevent endplate damage by the distractive force. In the event of spondylolisthesis the insertion instrument will be modified such that the blade lengths between the vertebrae will differ. The inferior blade 60.2 will be shorter than the superior blade 60.1 to avoid being placed beyond the anterior margin of the bottom vertebra.

The step of advancing the cage 10 along the blades 60.1, 60.2 further includes using the insertion instrumentation 58 described above. The threaded anterior end 74.1 of the rod 74 is screwed into the corresponding threaded hole carried by wall of the anterior 14 or posterior 16 end the cage 10. It is envisaged that by engaging the rod 72 with the anterior wall of the cage 10 may aid directional stability during advancement and placement of the cage. The rod 74 is attached to the cage 10 by gripping the head 74.3 and rotating it in a direction threading the rod 74 into the cage 10. Preferably, the bone graft material is packed in the cage 10 before attaching the rod 74 to the cage 10, and thus before placing the cage in the disc space. It is however envisaged that some bone graft may be placed after cage placement in the disc space through the threaded opening in the cage 10. It should be understood that the length of the rod 74, and in particular the distance by which it exceeds the length of the cylinder 72, is dependent on whether the rod 74 is attached to the anterior or posterior wall of the cage 10. A selection between rods of different lengths will be made in use.

Next, the cylinder 72 is threaded through the threaded opening in the end-plate 68. The cylinder 72 is typically rotated by using the handles 72.4 located at its posterior end 72.2. The cylinder 74 is rotated until the anterior end 72.1 of the cylinder makes contact with the back of the cage 10. The cylinder 72 is threaded further to drive the cage 10 along the insertion direction 76. The optional thrust member 78 may be located about the anterior end portion of the rod 74 such that it is held captive between the cage 10 and anterior end 72.1 of the cylinder 72. It should be understood that the cylinder 72 is rotated to drive the cage 10 until the cage is located in position in the disc space between the vertebrae.

Once the cage 10 is located at is desired position, the rod 74 is disconnected from the cage 10. Next, the stop 80 is rotated further in order to drive it along and relative to the cylinder 72 in a direction towards its anterior end 72.1, i.e. against the insertion tube 82. Due to the axial movement of the stop 80 being prevented by the insertion tube 82, the continued rotation of the stop 80 exerts an extraction force on the cylinder 72 and, accordingly, the blade structure 62. Through controlled rotation of the stop 80 the insertion instrumentation is slowly and under controlled conditions pulled back from inside the disc space with the cage 10 remaining in position. It should be understood that, although the rod 74 is disconnected from the cage 10 is remains attached to the thrust member 78 in order to ensure that the thrust member is retracted or removed with the rest of the instrumentation.

Prior to rotating the stop 80 to remove the blade structure 70 from the patient, the head 72.3 may be removed to ease turning of limit stop. This step is optional and intended to facilitate access to the stop 80.

It is envisaged that in some instances the attachment of the insertion tube 82 that attaches to a flexible arm (which is changed to rigid after correct positioning of the insertion tube) connected to the operating table may obstruct free movement of the stop 80 against the edge of the insertion tube 82. If this occurs, a cylindrical fitting may be inserted into the insertion tube before placement of the insertion instrumentation into the insertion tube 82. The fitting preferably engages the end of the insertion tube 82 such that it rests against the posterior edge of the insertion tube 82. The fitting will then provide a smooth surface or edge that facilitates rotation of the stop 80 during extraction of the instrument from the patient.

After removal of the insertion instruments from the patient placement of either i) pedicle screw instrumentation and reduction of listhesis, if present, or ii) fixation screws in the cage, if a standalone screw cage is used without listhesis. In the event of using a standalone screw cage with listhesis, the method may include placement of a superior cage screw, placement of the reduction instrument, reduction of the listhesis and placement of the inferior cage screw to complete fixation. More about this is said below.

Once the cage 10 is in place between the vertebrae and the instrumentation removed from the patient, additional bone graft material may be inserted into the internal volume 28 of the cage 10 through the traded opening in the cage. With the cage 10 in place between the vertebrae the remaining volume of the disc space is packed with bone grant material, if space allows this. It is envisaged that most of the bone outside the cage 10 will be packed in the disc space towards the lateral margins of the disc space but not in the space to be occupied by the cage. Contact is allowed between the bone graft material inside the cage 10 and the bone graft material outside the cage through the windows 30.

It should be understood that the method above was described with reference to a TLIF cage, which is placed posteriorly. The method of placing an ALIF (anterior lumbar interbody fusion) or cervical cage is essentially the same but performed by placing the cage anteriorly. The described process is therefore essentially the same but performed from the opposite direction. The size of the insertion instrumentation may vary as it is envisaged that it will be larger in for ALIF procedures and smaller for cervical procedures.

The insertion instrumentation of the invention allows for a method of inserting the cage 10 in the disc space without the use of a hammer to advance the cage. The advantage of this method is that it reduces the risk of the cage 10 suffering damage during advancement of the cage. The method is furthermore safer than known methods as it poses reduced risk of nerve or vertebral bone damage.

It should be understood the method of inserting a TLIF cage is carried out at an insertion angle, typically between 20° and 30°, due to the dural sac. It should therefore be understood that the TLIF placement procedure is not carried out directly from behind but instead at the insertion angle. ALIF and cervical cage placement may be carried out with an insertion angle of zero due to the dural sac being behind the cage during the procedure.

Figure 20:
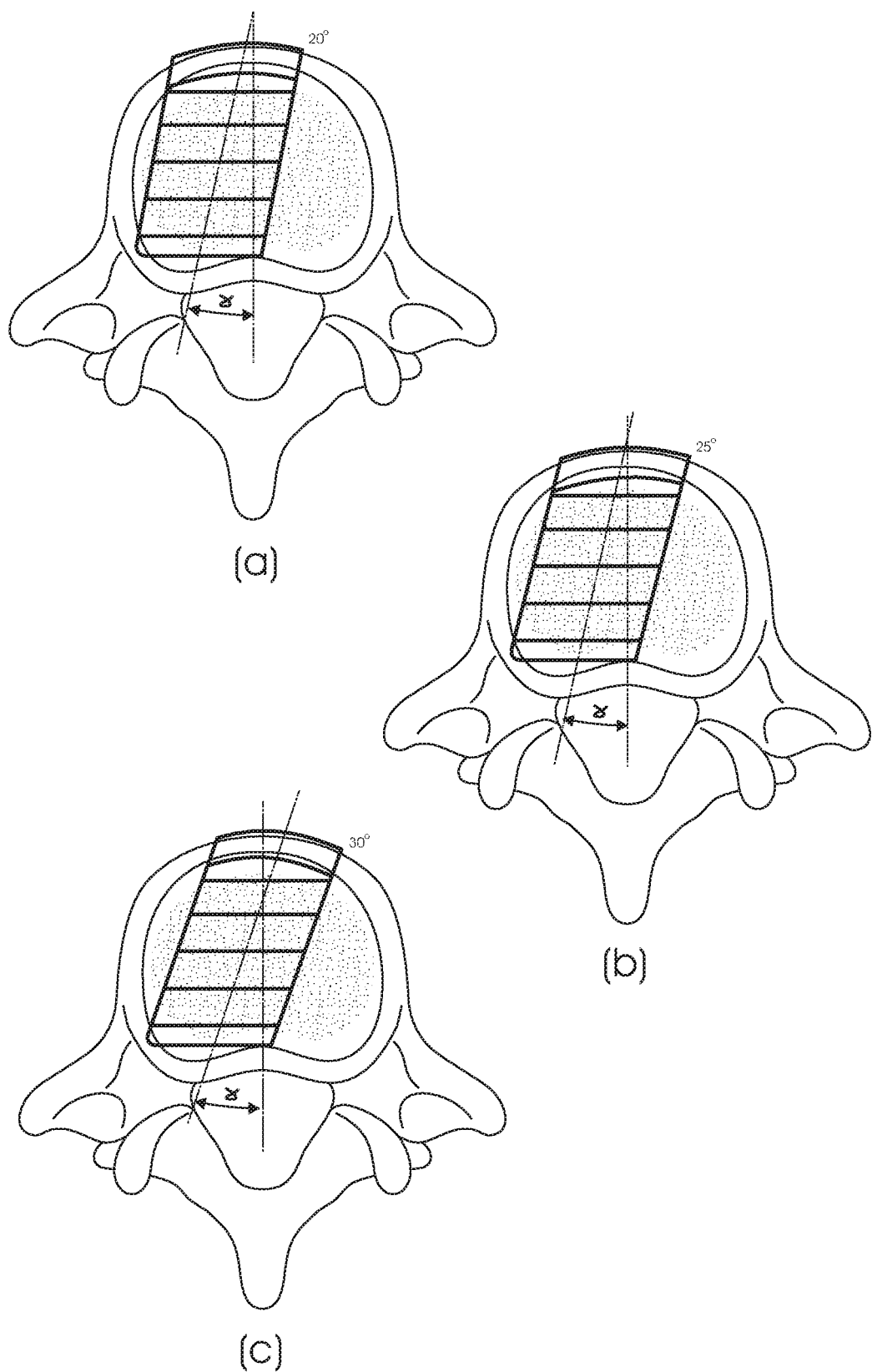
FIG. 20 shows a top view of alternative embodiments of a cage in accordance with the invention in (a), (b) and (c) respectively.
Figure 21:
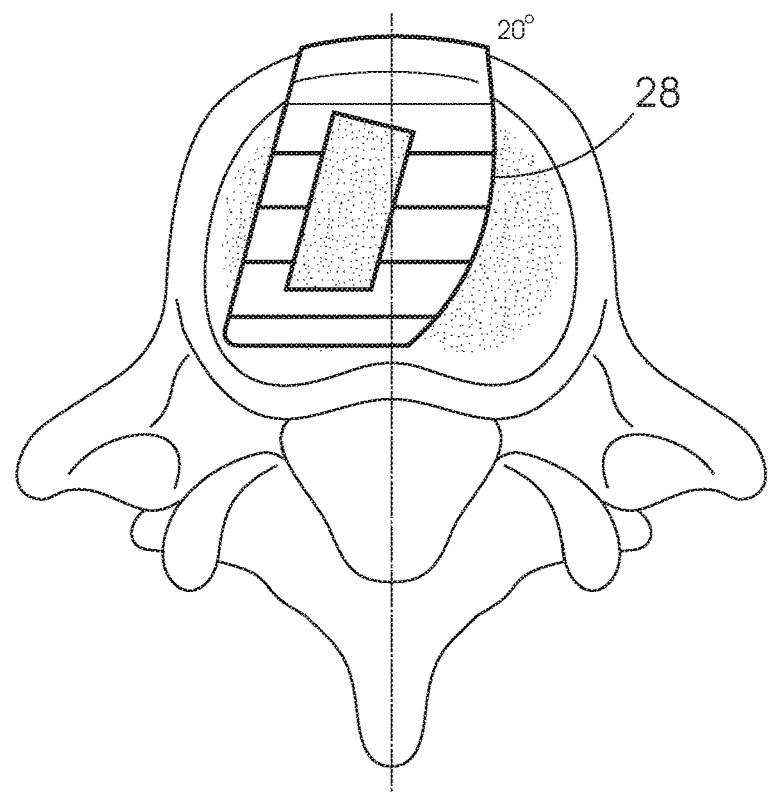
FIG. 21 shows a top view of an alternative embodiment of a cage in accordance with the invention in which one of its sides is convex.

FIG. 20(a) to (c) show typical cage 10 shapes for an angle of insertion δ ranging between 20° and 30°. As can be seen in the figures the areas of support of the cage 10 vary according to the angle of insertion. The most important area of support is between the anterior cortical rim and, ideally, with equal length of cage 10 on each side of the midline of the vertebrae. In order to improve the support between the vertebrae one side 28 of the cage could be convex so as to increase the size of the section of the cage 10 which is, in use, located on the right hand side as illustrated in FIG. 21.

Figure 22:
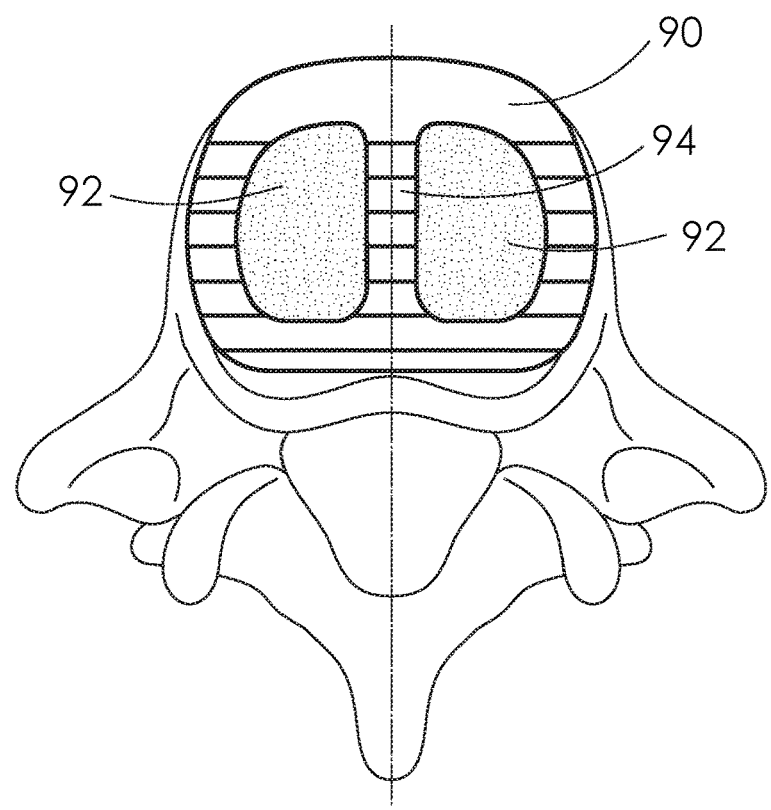
FIG. 22 shoes a top view of an alternative embodiment of a cage in accordance with the invention to be used as an AILF cage.
Figure 23:
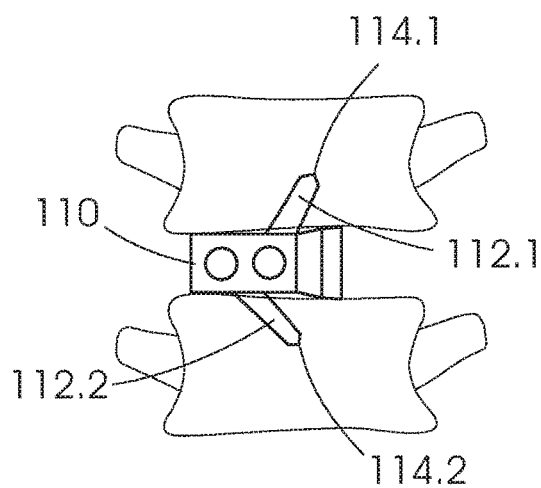
FIG. 23 shows a posterior schematic view of a TLIF cage with screw fixation in vertebral bodies.
Figure 24:
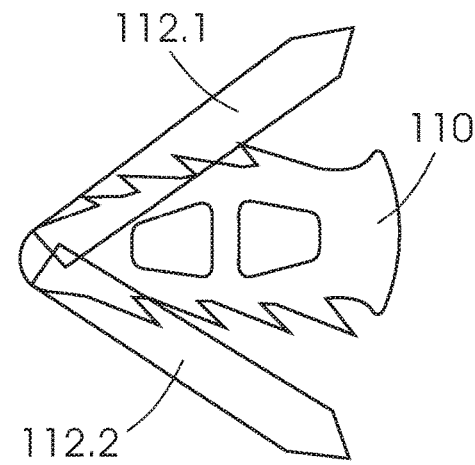
FIG. 24 shows a schematic side view of the TLIF cage of FIG. 27 with screws.
Figure 25:
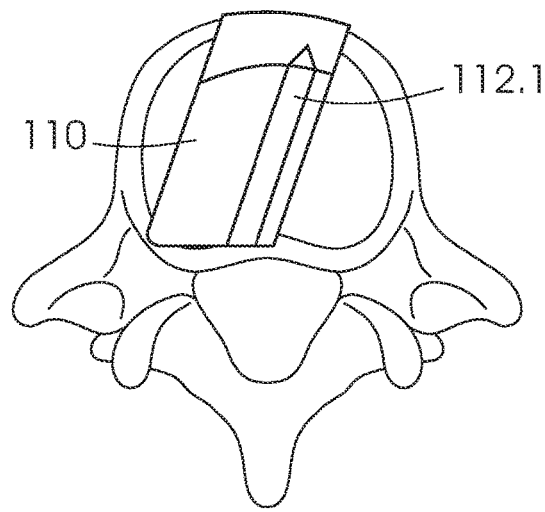
FIG. 25 shows a schematic top view of the TLIF cage of FIG. 27 in the bottom vertebra.
Figure 26:
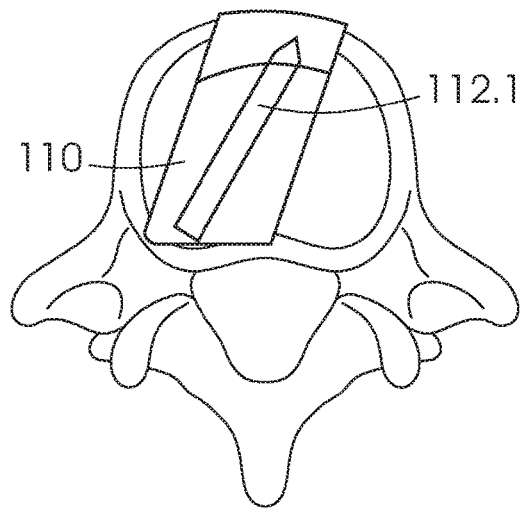
FIG. 26 shows a schematic top view of the TLIF cage of FIG. 27 in the top vertebra.

FIG. 22 shows an example of an AIIF cage 90 according to the invention. The AILF cage 90 is substantially similar to the cage 10. As shown in FIG. 22 the AILF cage is superior in size. The cage 90 shown in FIG. 22 has two openings 92 on either size of a central column 94. It is envisaged that a cervical cage according to the invention will have a similar shape to the AILF cage 90.

From the above description it should be understood that the intervertebral fusion cage 10 in accordance with the invention addresses the risk of cage subsidence. The cage 10 is shaped to complement the anatomical shape of the vertebra so as to avoid gaps in contact between the cage and vertebrae and to ensure that substantially the entire surface of the cage 10 makes contact with the vertebrae. The cage 10 is therefore shaped for superior engagement with the vertebrae so as to provide improved support and a more even load distribution on the cage 10. The cage 10 further locates relative to the vertebrae and engages the cortical bone of the vertebrae endplates, thereby reducing the risk of subsidence through the weaker cancellous part of the vertebra endplates. The cage 10 further improves the ability to restore and maintain height and lordosis of the intervertebral space. The pillar 40 provides superior support between the vertebra by engaging the cortical rim of bone of both the vertebrae above and below the cage 10. It is further believed that the cage 10 also stabilises the fused vertebrae better than known cages thereby increasing the likely success rate of fusion to occur. The serrations 46, 48 substantially prevent or decrease potential sliding movement of the top vertebra relative to the lower vertebra either through forward translation movement of the top vertebra as in spondylolisthesis or backwards movement of the bottom vertebra. The cage 10 therefore allows for the reduction of a spondylolisthesis with correct movement of the cage 10 and vertebrae in relation to each other during the act of reduction of the listhesis. With reference to FIG. 14, the segmental fusion and cage 10 will experience contact $F_1$, sliding $F_2$ and compression $F_3$ forces which could result in failed surgery. However, the fusion cage 10 of the invention is ideally suited to counter both compressive $F_2$ and shear $F_2$ forces as a result of the strong anterior column of the cage 10 resting on the cortical rims of the vertebrae, which counteracts the compressive force better with less risk of cage subsidence, and opposite facing surface teeth 46, 48, which counteract shear forces much better preventing vertebral slip or recurring listhesis post-fusion, maintenance of listhesis reduction and decreased translational motion with less risk of non-union. It is also believed that the design of the cage 10 will allow a surgeon to achieve more accurately the correct and required lordosis calculated for a given segment based on sagittal spino-pelvic parameters and type of Roussouly spinal shape. The correct and required lordosis for each patient is different based on his or her Roussoully curve, spinopelvic parameters and the loss of lordosis due to pathology. By correctly calculating required lordosis for each patient and more importantly correctly correcting this with surgery optimal short and long term outcome can be achieved.

It should be understood from the above description that the cage 10 of the invention could effect fusion and reduction of listhesis without the use of pedicle screw instrumentation, i.e. as a standalone cage.

In certain applications some modifications may be required when using the cage 10 as a standalone cage. For example, one of the modifications that may be required could be integral screw fixation of the cage. This modification may be made to ALIF, LLIF, TLIF and cervical cages. An example of a TLIF cage comprising integral screw fixation is shown in FIGS. 23 to 28 and indicated by the reference sign 110. The cage 110 is substantially identical to the cage 10 apart from the integral screw fixation and, accordingly, only the aspects relating to the integral screw fixation will be described in detail.

Figure 27:
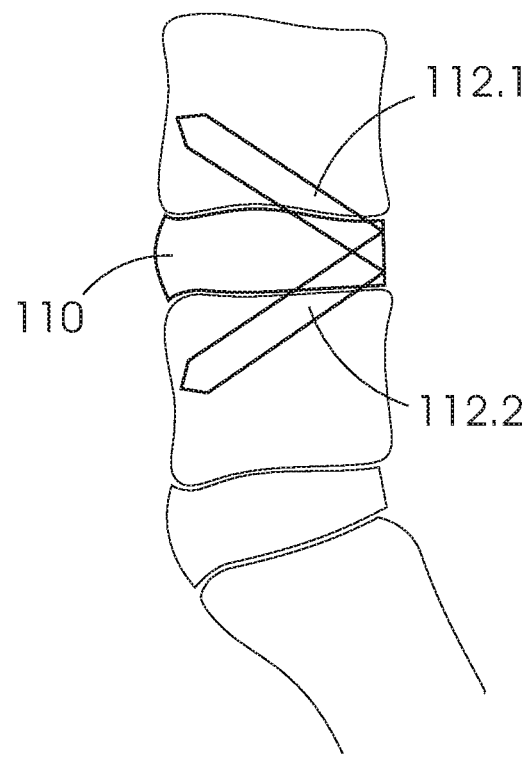
FIG. 27 shows a schematic side view of the TLIF cage of FIG. 27 located between vertebra.
Figure 28:
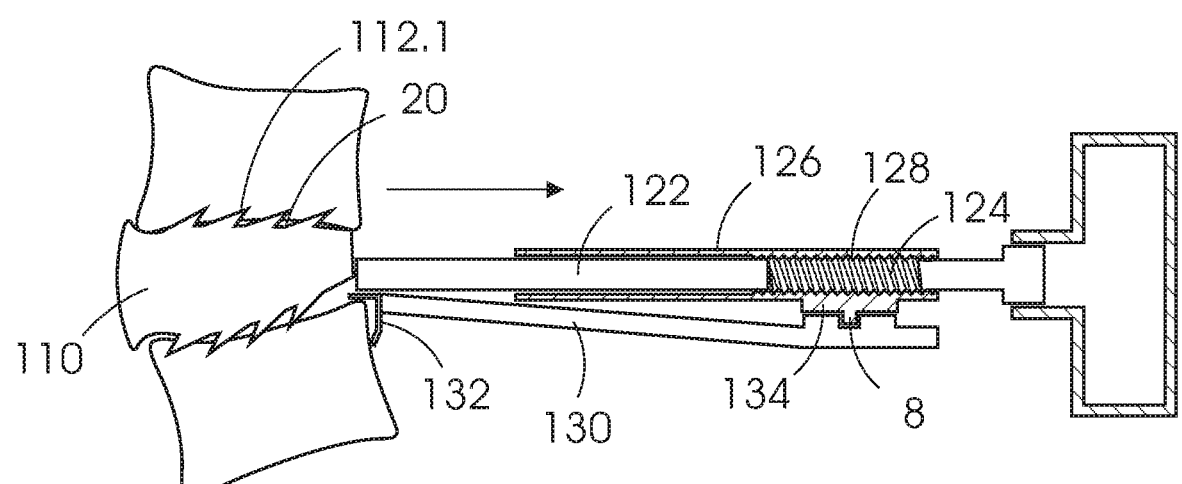
FIG. 28 shows a schematic side view of a spondylolisthesis reduction tool in use engaging the TLIF cage of FIG. 27.

The posterior end of the cage 110 is modified to allow two screws 112.1 and 112.2, which are angled relative to the anterior-posterior axis of the cage, to pass into the vertebral body above and below the cage. FIG. 27 shows the two screw projecting from the body of the cage 110. The first screw 112.1 is also referred to as a top screw while the second screw 112.2 is referred to as a bottom screw. Best seen in FIG. 28, the angle at which the screws extend when viewed from the side is between about 25 and about 35°. This angle is measured relative to a plane in which a disc lies when viewed from the side. When viewed from behind as shown in FIG. 27 or from the top/bottom as shows in FIGS. 29 and 30, the screws 112.1, 112.2 angle medially, i.e. inwardly. Referring in particular to FIG. 27, the first screw 112.1, which is the inside or medial screw, angles upward into the top vertebra and medially at about the same angle as the cage, e.g. between about 20° and 30°. The second screw 112.2, which is the lateral or outside screw, angles downward into the bottom vertebra and medially at an angle greater than the angle of the screw 112.1, e.g. between about 30° and 40° in order to attain or cross the midline of the vertebra. The free ends 114.1 and 114.2 of the screws 112.1, 112.2 are thus in a similar sagittal plane when viewed from behind or in front. The top screw 112.1 is located medially because insertion will be easier with the medial edge of dura and the next level exiting nerve root safer retracted. The bottom screw 112.2 insertion will also not be impeded by the next level nerve root.

In this particular embodiment, the length of the screws 112.1, 112.2 are typically be between about 25 and 40 mm. The diameter of the screws 112.2, 112.2 are typically between about 4 and 6 mm, typically about 5 mm. The thread depth and thread pitch of the screws 112.1, 112.2 may vary depending on the application. Increasing thread depth and decreasing thread pitch increases pull out strength in cancellous bone. The screw material may vary with options being titanium, titanium coated carbon fibre, PEEK or titanium plasma coated PEEK.

Each of the screws 112.1, 112.2 may contain a lag element below the screw head in order to pull the vertebra tightly onto the cage 110. It is envisaged that this will further improve the lordosis. It is further envisaged that the channels through which the screws 112.1, 112.2 pass in the cage 110 may be threaded so as to receive a thread on the outside of the screw head to reduce, and preferably prevent, screw back-out from the cage 110 and increase the force with which the screws are attached to the cage 110.

The superior screw 112.1 may further have a polyaxial head to allow attachment to a reduction instrument with a complimentary thread to an outer surface screw head thread. This will be required during reduction of a listhesis but will not be required in a non-listhetic fusion. The polyaxial head is therefore optional.

In use, with cage placement in spondilolisthesis the cage 110 would be placed in the final position in relation to the top vertebral endplate and fixated in this position by the top or superior screw 112.1. The head of the screw will remain outside the cage 110 for attachment to a reduction instrument 120 shown in FIG. 28.

The reduction process includes applying a pulling force on the top vertebra via the screw head and applying a pushing force on the bottom posterior superior edge of the vertebra. It is envisaged that the reduction instrument 120 could include an elongate engagement member in the form of a rod 122 carrying an external thread 124. The rod 122 is located rotationally within an outer cylinder 126 carrying a complimentary, internal thread 128. The externally threaded rod 122 is, in use, attached to the top screw head. A second elongate engagement member in the form of a second rod 130 carrying a vertebra engagement formation 132 for engaging the inferior vertebra posterior endplate ridge. The formation 132 could be in the form of a flat angled bar that in use rests on the inferior vertebra posterior superior endplate ridge. The cylinder 126, in particular its exterior surface, carries an engagement member 134 for engaging a complementary shaped engagement formation 136 carried by the bottom vertebra rod 130. The engagement formation 134 has a flat surface on which a short cylindrical male protrusion 138 is located preferably in the centre of the flat surface. In use, the male protrusion 138 is received in a female formation in the form of a recess or hole 140 formed on a complementary shaped flat surface located on the bottom vertebra rod. Engagement between the male protrusion 138 and female hole 140 attaches the cylinder 126 and rod 130 to each other to prevent relative movement between them. In other words, the cylinder 126 and rod 130 are connected in an immoveable rigid fashion at a point outside the tube. In should be understood that by rotating the threaded rod 122 inside the threaded cylinder 126 on the screw 112.1 inside the top vertebra a pulling force could be exerted on the top vertebra in relation to the bottom vertebra. In use, this action will pull back the top vertebra and "push" forward the bottom vertebra in relation to each other (Newton's third law). It is envisaged that the cage vertebra position of the superior cage surface 20 and superior vertebra will be fixed in the final position by cage placement and preliminary screw fixation prior to reduction. Due to the forward facing teeth 48 of the inferior cage surface 22 the bottom vertebra will slide forward in relation to the cage 110 and the superior vertebra. This will occur in a ratchet like fashion with engagement of the cage teeth 48 on the bottom vertebra endplate with each reduction movement and force applied. With completed reduction of the listhesis the bottom screw 112.2 will be placed through the cage 110 and into the bottom vertebra and the top screw will be tightened finally.

An alternative method of performing reduction may include using a reduction instrument comprising a double rack and pinion type mechanism.

Irrespective of the type of reduction instrument, it should be clear that, if no listhesis is present pre-operatively, the above reduction procedure is not required and the cage 110 can be fixated to the vertebrae directly after final cage placement position is achieved. With adequate height restoration by placing the cage listhesis is also reduced but not completely. Final reduction can the performed by using the reduction instrument 120 described above. The posterior surface of the cage 110 will thus be modified in the stand alone variant of the cage to receive the screws. In this standalone variation the bone will be placed in the cage 110 before insertion into the disc space. It is envisaged that the insertion instrument would require modifications to allow impact to the back of the cage 110.

It is believed that, in addition to the above-mentioned advantage of the cage 10, 110 of the present invention, particularly in standalone use, there could be further advantages, particularly to the patient. For example, the cage 10 could reduce post-op pain, shorten hospital stay, minimise para spinal muscle damage, result in significant cost saving, improve patient outcome and satisfaction, shorter operative time for fusion and decrease radiation exposure to patent and surgeon during surgery by not having to use X-ray fluoroscopy which is required when placing pedicle screw instrumentation during the minimal invasive technique specifically. Although X-ray fluoroscopy may be required during placement of screws in the cage to determine correct direction and length, will be to a much smaller degree than with pedicle screws.

It will be appreciated that the above description only provides some embodiments of the invention and that there may be many variations without departing from the spirit and/or the scope of the invention. It is easily understood from the present application that the particular features of the present invention, as generally described and illustrated in the figures, can be arranged and designed according to a wide variety of different configurations. In this way, the description of the present invention and the related figures are not provided to limit the scope of the invention but simply represent selected embodiments.

The skilled person will understand that the technical characteristics of a given embodiment can in fact be combined with characteristics of another embodiment, unless otherwise expressed or it is evident that these characteristics are incompatible. Also, the technical characteristics described in a given embodiment can be isolated from the other characteristics of this embodiment unless otherwise expressed.

The invention claimed is:

1. An intervertebral fusion cage for insertion between vertebrae, the cage including:
   a body defining a first, anterior portion, a second, posterior portion and a central portion extending between the anterior and posterior portions;
   wherein the central portion defines a first surface which is, in use, a top surface and a second surface which is, in use, a bottom surface, the top and bottom surfaces carrying gripping formations for gripping end plates of the vertebrae;
   wherein the gripping formations on the top and bottom surfaces face substantially opposite directions such that the gripping formations on the top surface obstruct movement in a first direction while the gripping formations on the bottom surface obstruct movement in a second direction, which is substantially opposite the first direction; and
   an engagement formation carried by the anterior portion of the body, wherein the engagement formation has concave upper and lower surfaces for complemental engagement with the cortical rims for the vertebrae located in use above and below the cage, and wherein the concave upper and lower surfaces define concavities in which the cortical rims of the upper and lower vertebrae are, in use, received.

2. An intervertebral fusion cage according to claim 1, wherein the gripping formations are in the form of upstanding serrations located on the top and bottom surfaces respectively.

3. An intervertebral fusion cage according to claim 2, wherein the serrations are arranged as a series of parallel serrations which are spaced apart by intermediate sections located between adjacent serrations.

4. An intervertebral fusion cage according to claim 1, including a pillar carried by the anterior portion of the body for providing support between the vertebrae so as to prevent the cage from collapsing in use.

5. An intervertebral fusion cage according to claim 4, wherein the pillar is defined by the anterior portion and forms part of the engagement formation.

6. An intervertebral fusion cage according to claim 5, wherein the pillar is formed between the upper and lower concave surfaces of the engagement formation.

7. An intervertebral fusion cage according to claim 1, including an internal cavity for receiving bone graft material, wherein the cavity is open to the top and/or bottom surfaces of the body.

8. An intervertebral fusion cage according to claim 7, wherein the cage carries openings in cage side walls extending between anterior and posterior ends of the cage, the openings being in communication with the internal cavity such that, in use, the bone graft material inside the internal cavity may be in contact with bone graft material in the disc space by means of the openings.

9. An intervertebral fusion cage according to claim 1, wherein the cage is tapered from an anterior end to a posterior end at a taper angle of between about 0° and about 20°.

10. A method of inserting an intervertebral fusion cage according to claim 1 into a disc space located between vertebrae of a patient, the method including the following steps:

placing the intervertebral fusion cage between a pair of thin metal blades each having a smooth surface;

inserting the blades into the disc space between the vertebrae;

advancing the cage between the metal blades in an insertion direction towards the disc space by sliding serrations of the cage along the smooth surfaces of the blades;

positioning the cage between the vertebrae such that the anterior cortical rims of the vertebrae between which the cage is placed are received in the upper and lower concavities, thereby locating the cage relative to the vertebrae;

substantially preventing translational movement of the vertebrae, in both an an anterior direction and a posterior direction, relative to the cage and relative to each other by engaging the end plates of the vertebrae with the gripping formations located on the top and bottom surfaces of the cage; and withdrawing the blades from the disc space.

11. A method according to claim 10, wherein the step of advancing the cage between the blades includes the steps of:

attaching an attachment tool to the cage;

connecting a drive tool to a blade structure comprising the blades; and moving the drive tool relative to the blade structure to impart a driving force to the cage in order to drive it along the insertion direction.

12. A method according to claim 11, wherein the step of attaching the attachment tool to the cage includes threading an anterior end of the attachment tool to an anterior wall or a posterior wall of the cage.

13. A method according to claim 11, wherein the step of connecting the drive tool to the blade structure includes threading the drive tool through a threaded socket carried by the blade structure such that an anterior end of the drive tool extends through the socket.

14. A method according to claim 13, wherein the step of moving the drive tool relative to the blade structure includes rotating the drive tool to thread in further past the threaded socket into the blade structure.

15. A method according to claim 14, including limiting the movement of the blade structure in the insertion direction by adjusting an adjustable stop until it impacts a posterior end of an insertion tube used in the insertion of the cage into the disc space.

16. A method according to claim 15, wherein step of withdrawing the blades from the disc space includes moving the adjustable stop relative to the drive tool to remove the blades in a continuous and controlled manner.

17. A method according to claim 10, including the following steps:

inserting bone graft material in an internal cavity of the cage before inserting the cage between the vertebrae and inserting additional bone graft material into the cage after placement of the cage in the disc space;

packing the remaining volume of the disc space with bone grant material; and allowing contact between the bone graft material inside the cage and the bone graft material outside the cage through openings in side walls of the cage.

18. A method according to claim 10, including widening a working corridor through which the disc space is entered so as to offer better vision into the disc space and allow it to be cleaned out satisfactorily, wherein the step of widening the corridor includes the following steps:

placing a tube on the facet and lamina of one of the vertebrae;

drilling the vertebral lamina and facet away and relieving any stenosis of the lateral recess, central canal and foramen;

developing the disc space between the dura medially and the exiting nerve root in the foramen laterally;

incising the annulus of the disc and flapping it upward and medially towards the dura;

taking the flap up to the midline or across to the contralateral side, if possible;

cutting the flap as broad as possible even if the disc space is narrow and collapsed; and placing a stay suture through the lateral margin of the flap and taking it outside the tube and attaching it to an artery forceps which hangs free on the side of the patient performing mild continuous retraction of the dura and roots medially.

19. A method according to claim 10, further including the following steps:

removing the overhanging posterior rim of the endplate of the vertebra above and below the disc space up to and across the midline, if possible; and loosening the annulus further across the midline.

* * * * *